(12) United States Patent
Levy et al.

(10) Patent No.: US 10,470,649 B2
(45) Date of Patent: Nov. 12, 2019

(54) REMOVABLE TIP ENDOSCOPE

(71) Applicant: EndoChoice Innovation Center Ltd., Caesarea (IL)

(72) Inventors: Avi Levy, Herzliya (IL); Moshe Levi, Ganey Tikva (IL); Amram Aizenfeld, Ramot Menashe (IL)

(73) Assignee: EndoChoice, Inc., Alpharetta, GA (US)

( * ) Notice: Subject to any disclaimer, the term of this patent is extended or adjusted under 35 U.S.C. 154(b) by 212 days.

(21) Appl. No.: 15/491,811

(22) Filed: Apr. 19, 2017

(65) Prior Publication Data

US 2017/0280975 A1    Oct. 5, 2017

Related U.S. Application Data

(63) Continuation of application No. 13/713,449, filed on Dec. 13, 2012, now Pat. No. 9,655,502.

(60) Provisional application No. 61/569,796, filed on Dec. 13, 2011.

(51) Int. Cl.
| | |
|---|---|
| *A61B 1/05* | (2006.01) |
| *A61B 1/00* | (2006.01) |
| *A61B 1/06* | (2006.01) |
| *A61B 1/018* | (2006.01) |
| *A61B 1/12* | (2006.01) |

(52) U.S. Cl.
CPC .......... *A61B 1/053* (2013.01); *A61B 1/00045* (2013.01); *A61B 1/00105* (2013.01); *A61B 1/00114* (2013.01); *A61B 1/00181* (2013.01); *A61B 1/018* (2013.01); *A61B 1/0676* (2013.01); *A61B 1/00091* (2013.01); *A61B 1/00124* (2013.01); *A61B 1/0638* (2013.01); *A61B 1/126* (2013.01)

(58) Field of Classification Search
CPC ............ A61B 1/00101; A61B 1/00105; A61B 1/00174; A61B 1/00177; A61B 1/00179; A61B 1/00181; A61B 1/00183
USPC ......................... 600/112, 170, 172, 177, 183
See application file for complete search history.

(56) References Cited

U.S. PATENT DOCUMENTS

| | | |
|---|---|---|
| 3,639,714 A | 2/1972 | Fujimoto |
| 3,955,064 A | 5/1976 | Demetrio |
| 4,037,588 A | 7/1977 | Heckele |
| (Continued) | | |

FOREIGN PATENT DOCUMENTS

| | | |
|---|---|---|
| CN | 1376443 | 10/2002 |
| CN | 2829646 Y | 10/2006 |
| (Continued) | | |

OTHER PUBLICATIONS

Brochure for US Endoscopy's AquaShield Water Bottle System, 2010.

(Continued)

*Primary Examiner* — Timothy J Neal
*Assistant Examiner* — Jae Woo
(74) *Attorney, Agent, or Firm* — Bookoff McAndrews, PLLC

(57) ABSTRACT

There is provided herein, an endoscope comprising an elongated shaft terminating with a tip section wherein said tip section comprises a permanent section connected to the elongated shaft and a removable section securely connectable to the permanent section, wherein the removable section comprises at least one capture device and at least one light source.

18 Claims, 6 Drawing Sheets

(56) References Cited

U.S. PATENT DOCUMENTS

| | | | |
|---|---|---|---|
| 4,084,401 A | 4/1978 | Beiardi | |
| 4,253,448 A | 3/1981 | Terada | |
| 4,261,345 A | 4/1981 | Yamaguchi | |
| 4,402,313 A | 9/1983 | Yabe | |
| 4,414,608 A | 11/1983 | Furihata | |
| 4,439,030 A | 3/1984 | Ueda | |
| 4,469,090 A | 9/1984 | Konomura | |
| 4,494,549 A | 1/1985 | Namba | |
| 4,522,196 A | 6/1985 | Cunningham | |
| 4,565,423 A | 1/1986 | Ueda | |
| 4,576,144 A | 3/1986 | Ishii | |
| 4,588,294 A | 5/1986 | Siegmund | |
| 4,590,923 A | 5/1986 | Watanabe | |
| 4,641,635 A | 2/1987 | Yabe | |
| 4,660,982 A * | 4/1987 | Okada | A61B 1/00096 356/636 |
| 4,699,463 A | 10/1987 | D'Amelio | |
| 4,708,126 A | 11/1987 | Toda | |
| 4,727,859 A * | 3/1988 | Lia | A61B 1/00101 356/241.5 |
| 4,736,732 A | 4/1988 | Shimonaka | |
| 4,753,222 A | 6/1988 | Morishita | |
| 4,764,001 A | 8/1988 | Yokota | |
| 4,794,913 A | 1/1989 | Shimonaka | |
| 4,801,792 A | 1/1989 | Yarnasita | |
| 4,841,952 A | 6/1989 | Sato | |
| 4,846,154 A | 7/1989 | MaCanally | |
| 4,868,644 A | 9/1989 | Yabe | |
| 4,877,314 A | 10/1989 | Kanamori | |
| 4,878,485 A | 11/1989 | Adair | |
| 4,888,639 A | 12/1989 | Yabe | |
| 4,902,115 A | 2/1990 | Takahashi | |
| 4,905,670 A | 3/1990 | Adair | |
| 4,914,521 A | 4/1990 | Adair | |
| 4,974,075 A | 11/1990 | Nakajima | |
| 4,976,522 A | 12/1990 | Igarashi | |
| 4,982,724 A | 1/1991 | Saito | |
| 4,984,878 A | 1/1991 | Miyano | |
| 4,998,182 A | 3/1991 | Krauter | |
| 5,166,787 A | 11/1992 | Irion | |
| 5,193,525 A | 3/1993 | Silverstein | |
| 5,239,983 A | 8/1993 | Katsurada | |
| 5,296,971 A | 3/1994 | Mori | |
| 5,299,561 A | 4/1994 | Yoshimoto | |
| 5,305,121 A | 4/1994 | Moll | |
| 5,309,227 A | 5/1994 | Inoue | |
| 5,313,934 A | 5/1994 | Wiita | |
| 5,339,800 A | 8/1994 | Wiita | |
| 5,359,456 A | 10/1994 | Kikuchi | |
| 5,380,049 A | 1/1995 | Smowton | |
| 5,398,056 A | 3/1995 | Yabe | |
| 5,408,623 A | 4/1995 | Dolidon | |
| 5,412,478 A | 5/1995 | Ishihara | |
| 5,420,644 A | 5/1995 | Watanabe | |
| 5,432,543 A | 7/1995 | Hasegawa | |
| 5,436,767 A | 7/1995 | Suzuki | |
| 5,447,148 A | 9/1995 | Oneda | |
| 5,452,391 A | 9/1995 | Chou | |
| 5,460,167 A | 10/1995 | Yabe | |
| 5,475,420 A | 12/1995 | Buchin | |
| 5,483,951 A | 1/1996 | Frassica | |
| 5,485,316 A | 1/1996 | Mori | |
| 5,489,256 A | 2/1996 | Adair | |
| 5,507,717 A | 4/1996 | Kura | |
| 5,512,940 A | 4/1996 | Takasugi | |
| 5,515,449 A | 5/1996 | Tsuruoka | |
| 5,518,501 A | 5/1996 | Oneda | |
| 5,518,502 A | 5/1996 | Kaplan | |
| 5,547,455 A | 8/1996 | McKenna | |
| 5,547,457 A | 8/1996 | Tsuyuki | |
| 5,550,582 A | 8/1996 | Takasugi | |
| 5,585,840 A | 12/1996 | Watanabe | |
| 5,587,839 A | 12/1996 | Miyano | |
| 5,589,874 A | 12/1996 | Buchin | |
| 5,592,216 A | 1/1997 | Uehara | |
| 5,605,530 A | 2/1997 | Fischell | |
| 5,609,560 A | 3/1997 | Ichikawa | |
| 5,617,136 A | 4/1997 | Iso | |
| 5,630,782 A | 5/1997 | Adair | |
| 5,653,677 A | 8/1997 | Okada | |
| 5,656,011 A | 8/1997 | Uihlein | |
| 5,662,588 A | 9/1997 | Iida | |
| 5,675,378 A | 10/1997 | Takasugi | |
| 5,679,110 A | 10/1997 | Hamazaki | |
| 5,685,823 A | 11/1997 | Ito | |
| 5,701,155 A | 12/1997 | Wood | |
| 5,702,345 A | 12/1997 | Wood | |
| 5,702,347 A | 12/1997 | Yabe | |
| 5,707,344 A | 1/1998 | Nakazawa | |
| 5,716,323 A | 2/1998 | Lee | |
| 5,725,474 A | 3/1998 | Yasui | |
| 5,725,476 A | 3/1998 | Yasui | |
| 5,725,477 A | 3/1998 | Yasui | |
| 5,728,045 A | 3/1998 | Komi | |
| 5,751,340 A | 5/1998 | Strobl | |
| 5,764,809 A | 6/1998 | Nomami | |
| 5,777,797 A | 7/1998 | Miyano | |
| 5,782,751 A | 7/1998 | Matsuno | |
| 5,793,539 A | 8/1998 | Konno | |
| 5,800,341 A | 9/1998 | McKenna | |
| 5,812,187 A | 9/1998 | Watanabe | |
| 5,830,124 A | 11/1998 | Suzuki | |
| 5,836,894 A | 11/1998 | Sarvazyan | |
| 5,852,511 A | 12/1998 | Tateyama | |
| 5,860,913 A | 1/1999 | Yamaya | |
| 5,870,234 A | 2/1999 | EbbesmeierneeSchitthof | |
| 5,871,439 A | 2/1999 | Takahashi | |
| 5,871,440 A | 2/1999 | Okada | |
| 5,876,326 A | 3/1999 | Takamura | |
| 5,879,284 A | 3/1999 | Tsujita | |
| 5,894,322 A | 4/1999 | Hamano | |
| 5,912,764 A | 6/1999 | Togino | |
| 5,913,817 A | 6/1999 | Lee | |
| 5,914,810 A | 6/1999 | Watts | |
| 5,916,148 A | 6/1999 | Tsuyuki | |
| 5,929,901 A | 7/1999 | Adair | |
| 5,930,424 A | 7/1999 | Heimberger | |
| 5,933,275 A | 8/1999 | Igarashi | |
| 5,933,282 A | 8/1999 | Tomioka | |
| 5,936,773 A | 8/1999 | Togino | |
| 5,940,126 A | 8/1999 | Kimura | |
| 5,961,445 A | 10/1999 | Chikama | |
| 5,969,888 A | 10/1999 | Sukekawa | |
| 5,986,693 A | 11/1999 | Adair | |
| 5,989,185 A | 11/1999 | Miyazaki | |
| 5,993,037 A | 11/1999 | Tomioka | |
| 5,993,467 A * | 11/1999 | Yoon | A61B 17/0469 606/147 |
| 5,995,136 A | 11/1999 | Hattori | |
| 6,009,169 A | 12/1999 | Schaack | |
| 6,025,873 A | 2/2000 | Nishioka | |
| 6,043,839 A | 3/2000 | Adair | |
| 6,069,698 A | 5/2000 | Ozawa | |
| 6,080,104 A | 6/2000 | Ozawa | |
| 6,104,540 A | 8/2000 | Hayakawa | |
| 6,110,127 A | 8/2000 | Suzuki | |
| 6,117,068 A | 9/2000 | Gourley | |
| 6,124,989 A | 9/2000 | Oode | |
| 6,139,175 A | 10/2000 | Tomioka | |
| 6,139,490 A | 10/2000 | Breidenthal | |
| 6,147,808 A | 11/2000 | Togino | |
| 6,163,401 A | 12/2000 | Igarashi | |
| 6,166,858 A | 12/2000 | Togino | |
| 6,181,481 B1 | 1/2001 | Yamamoto | |
| 6,184,923 B1 | 2/2001 | Miyazaki | |
| 6,185,046 B1 | 2/2001 | Togino | |
| 6,196,967 B1 | 3/2001 | Lim | |
| 6,201,646 B1 | 3/2001 | Togino | |
| 6,201,648 B1 | 3/2001 | Togino | |
| 6,210,322 B1 | 4/2001 | Byrne | |
| 6,211,904 B1 | 4/2001 | Adair | |
| 6,215,517 B1 | 4/2001 | Takahashi | |
| 6,217,500 B1 | 4/2001 | Helseth | |
| 6,245,086 B1 | 6/2001 | Storz | |

(56) References Cited

U.S. PATENT DOCUMENTS

| | | |
|---|---|---|
| 6,249,391 B1 | 6/2001 | Hayakawa |
| 6,260,994 B1 | 7/2001 | Matsumoto |
| 6,261,226 B1 | 7/2001 | McKenna |
| 6,275,255 B1 | 8/2001 | Adair |
| 6,295,368 B1 | 9/2001 | Hasegawa |
| 6,306,082 B1 | 10/2001 | Takahashi |
| 6,310,642 B1 | 10/2001 | Adair |
| 6,310,736 B1 | 10/2001 | Togino |
| 6,315,712 B1 | 11/2001 | Rovegno |
| 6,322,496 B1 | 11/2001 | Iida |
| 6,327,094 B1 | 12/2001 | Aoki |
| 6,327,101 B1 | 12/2001 | Miyano |
| 6,334,845 B1 | 1/2002 | Higuchi |
| 6,353,504 B1 | 3/2002 | Yamamoto |
| 6,375,610 B2 | 4/2002 | Verschuur |
| 6,387,045 B1 | 5/2002 | Takahashi |
| 6,398,723 B1 | 6/2002 | Kehr |
| 6,400,514 B2 | 6/2002 | Minami |
| 6,422,995 B2 | 7/2002 | Akiba |
| 6,425,857 B1 | 7/2002 | Rudischhauser |
| 6,436,045 B1 * | 8/2002 | Rafter ............... A61B 8/467 600/447 |
| 6,450,950 B2 | 9/2002 | Irion |
| 6,461,304 B1 | 10/2002 | Tanaka |
| 6,464,631 B1 | 10/2002 | Girke |
| 6,464,633 B1 | 10/2002 | Hosoda |
| 6,468,201 B1 | 10/2002 | Burdick |
| 6,468,202 B1 | 10/2002 | Irion |
| 6,471,636 B1 | 10/2002 | Sano |
| 6,471,637 B1 | 10/2002 | Green |
| 6,473,116 B1 | 10/2002 | Takahashi |
| 6,476,851 B1 | 11/2002 | Nakamura |
| 6,500,115 B2 | 12/2002 | Krattiger |
| 6,514,210 B2 | 2/2003 | Ohara |
| 6,520,908 B1 | 2/2003 | Ikeda |
| 6,527,704 B1 | 3/2003 | Chang |
| 6,530,881 B1 | 3/2003 | Ailinger |
| 6,533,722 B2 | 3/2003 | Nakashima |
| 6,545,703 B1 | 4/2003 | Takahashi |
| 6,551,239 B2 | 4/2003 | Renner |
| 6,554,767 B2 | 4/2003 | Tanaka |
| 6,567,114 B2 | 5/2003 | Takahashi |
| 6,569,084 B1 | 5/2003 | Mizuno |
| 6,582,361 B2 | 6/2003 | Hirano |
| 6,589,168 B2 | 7/2003 | Thompson |
| 6,606,113 B2 | 8/2003 | Nakamura |
| 6,618,205 B2 | 9/2003 | Murayama |
| D481,125 S | 10/2003 | Hayamizu |
| 6,638,212 B1 | 10/2003 | Oshima |
| 6,638,214 B2 | 10/2003 | Akiba |
| 6,641,531 B2 | 11/2003 | Kehr |
| 6,656,111 B2 | 12/2003 | Fujii |
| 6,671,099 B2 | 12/2003 | Nagata |
| 6,677,983 B1 | 1/2004 | Takahashi |
| 6,677,984 B2 | 1/2004 | Kobayashi |
| 6,677,992 B1 | 1/2004 | Matsumoto |
| 6,692,430 B2 | 2/2004 | Adler |
| 6,692,431 B2 | 2/2004 | Kazakevich |
| 6,699,181 B2 | 3/2004 | Wako |
| 6,699,185 B2 | 3/2004 | Gminder |
| 6,704,052 B1 | 3/2004 | Togino |
| 6,712,760 B2 | 3/2004 | Sano |
| D490,898 S | 6/2004 | Hayamizu |
| 6,764,439 B2 | 7/2004 | Schaaf |
| 6,778,208 B2 | 8/2004 | Takeshige |
| 6,788,343 B1 | 9/2004 | Togino |
| 6,793,621 B2 | 9/2004 | Butler |
| 6,801,325 B2 | 10/2004 | Farr |
| 6,809,499 B2 | 10/2004 | Solingen |
| 6,809,866 B2 | 10/2004 | Xie |
| 6,829,003 B2 | 12/2004 | Takami |
| 6,832,984 B2 | 12/2004 | Stelzer |
| 6,844,985 B2 | 1/2005 | Murayama |
| 6,846,311 B2 | 1/2005 | Gatto |
| 6,849,043 B2 | 2/2005 | Kondo |
| 6,860,516 B2 | 3/2005 | Ouchi |
| 6,876,380 B2 | 4/2005 | Abe |
| 6,887,194 B2 | 5/2005 | Hart |
| 6,888,119 B2 | 5/2005 | Iizuka |
| 6,898,066 B1 | 5/2005 | Takami |
| 6,899,673 B2 | 5/2005 | Ogura |
| 6,900,829 B2 | 5/2005 | Ozawa |
| 6,900,950 B2 | 5/2005 | Nagata |
| 6,902,529 B2 | 6/2005 | Onishi |
| 6,903,761 B1 | 6/2005 | Abe |
| 6,918,693 B2 | 7/2005 | Ota |
| 6,921,362 B2 | 7/2005 | Ouchi |
| 6,930,705 B2 | 8/2005 | Tanaka |
| 6,933,962 B2 | 8/2005 | Yamamoto |
| 6,937,267 B1 | 8/2005 | Takahashi |
| 6,937,269 B2 | 8/2005 | Sugimoto |
| 6,943,821 B2 | 9/2005 | Abe |
| 6,943,822 B2 | 9/2005 | Iida |
| 6,944,031 B2 | 9/2005 | Takami |
| 6,945,929 B2 | 9/2005 | Ando |
| 6,947,070 B2 | 9/2005 | Takami |
| 6,950,691 B2 | 9/2005 | Uchikubo |
| 6,956,703 B2 | 10/2005 | Saito |
| 6,967,673 B2 | 11/2005 | Ozawa |
| 6,977,670 B2 | 12/2005 | Takahashi |
| 6,980,227 B2 | 12/2005 | Iida |
| 6,982,740 B2 | 1/2006 | Adair |
| 6,985,170 B1 | 1/2006 | Tsuyuki |
| 6,992,694 B2 | 1/2006 | Abe |
| 6,995,786 B2 | 2/2006 | Abe |
| 6,997,871 B2 | 2/2006 | Sonnenschein |
| 7,027,231 B2 | 4/2006 | Miyano |
| 7,030,904 B2 | 4/2006 | Adair |
| 7,037,258 B2 | 5/2006 | Chatenever |
| 7,042,488 B2 | 5/2006 | Higuchi |
| 7,043,153 B2 | 5/2006 | Takeyama |
| 7,046,270 B2 | 5/2006 | Murata |
| 7,050,066 B2 | 5/2006 | Ozawa |
| 7,074,181 B2 | 7/2006 | Futatsugi |
| 7,074,182 B2 | 7/2006 | Rovegno |
| 7,085,064 B2 | 8/2006 | Uzawa |
| 7,097,615 B2 | 8/2006 | Banik |
| 7,104,951 B2 | 9/2006 | Hasegawa |
| 7,108,656 B2 | 9/2006 | Fujikawa |
| 7,108,657 B2 | 9/2006 | Irion |
| 7,119,830 B2 | 10/2006 | Saito |
| 7,123,288 B2 | 10/2006 | Abe |
| 7,128,709 B2 | 10/2006 | Saruya |
| 7,129,472 B1 | 10/2006 | Okawa |
| 7,133,063 B2 | 11/2006 | Abe |
| D534,656 S | 1/2007 | Pilvisto |
| 7,156,863 B2 | 1/2007 | Sonnenschein |
| 7,158,314 B2 | 1/2007 | Fujii |
| 7,179,221 B2 | 2/2007 | Tsujita |
| 7,180,686 B2 | 2/2007 | Kato |
| 7,218,454 B2 | 5/2007 | Miyano |
| 7,223,231 B2 | 5/2007 | Akiba |
| 7,231,135 B2 | 6/2007 | Esenyan |
| 7,232,409 B2 | 6/2007 | Hale |
| 7,233,820 B2 | 6/2007 | Gilboa |
| 7,242,833 B2 | 7/2007 | Yang |
| 7,248,281 B2 | 7/2007 | Abe |
| 7,248,296 B2 | 7/2007 | Iketani |
| 7,252,633 B2 | 8/2007 | Obata |
| 7,255,676 B2 | 8/2007 | Higuchi |
| 7,262,797 B2 | 8/2007 | Weldum |
| 7,267,647 B2 | 9/2007 | Okada |
| 7,273,452 B2 | 9/2007 | Barbato |
| 7,277,120 B2 | 10/2007 | Gere |
| 7,280,140 B2 | 10/2007 | Henderson |
| 7,280,283 B1 | 10/2007 | Kasai |
| 7,282,025 B2 | 10/2007 | Abe |
| 7,306,588 B2 | 12/2007 | Loeb |
| 7,330,749 B1 | 2/2008 | Bhunachet |
| D564,659 S | 3/2008 | Hayashi |
| D564,660 S | 3/2008 | Hayashi |
| 7,351,202 B2 | 4/2008 | Long |
| 7,355,625 B1 | 4/2008 | Mochida |
| 7,358,987 B2 | 4/2008 | Takeshige |

(56) References Cited

U.S. PATENT DOCUMENTS

| | | |
|---|---|---|
| 7,365,768 B1 | 4/2008 | Ono |
| 7,371,211 B2 | 5/2008 | Akiba |
| 7,379,252 B2 | 5/2008 | Murayama |
| 7,384,308 B2 | 6/2008 | Boehnlein |
| 7,399,304 B2 | 7/2008 | Gambale |
| 7,400,341 B2 | 7/2008 | Abe |
| 7,401,984 B2 | 7/2008 | Pattie |
| 7,409,130 B2 | 8/2008 | Hatori |
| 7,420,586 B2 | 9/2008 | Higuchi |
| 7,427,263 B2 | 9/2008 | Hoeg |
| 7,431,619 B2 | 10/2008 | Boehnlein |
| 7,435,217 B2 | 10/2008 | Wiklof |
| 7,435,218 B2 | 10/2008 | Krattiger |
| 7,440,005 B2 | 10/2008 | Enomoto |
| 7,443,488 B2 | 10/2008 | Ogawa |
| 7,450,151 B2 | 11/2008 | Kaneko |
| 7,466,490 B2 | 12/2008 | Igarashi |
| 7,471,310 B2 | 12/2008 | Amling |
| 7,484,709 B2 | 2/2009 | Efinger |
| 7,486,449 B2 | 2/2009 | Miyano |
| 7,492,388 B2 | 2/2009 | Odlivak |
| 7,514,667 B2 | 4/2009 | Matsumoto |
| 7,518,632 B2 | 4/2009 | Konomura |
| 7,530,948 B2 | 5/2009 | Seibel |
| 7,542,069 B2 | 6/2009 | Tashiro |
| 7,553,276 B2 | 6/2009 | Iddan |
| 7,559,889 B2 | 7/2009 | Takahashi |
| 7,559,892 B2 | 7/2009 | Adler |
| 7,561,351 B2 | 7/2009 | Konno |
| 7,569,012 B2 | 8/2009 | Tanaka |
| 7,573,499 B2 | 8/2009 | Doguchi |
| 7,576,310 B2 | 8/2009 | Konno |
| 7,581,988 B2 | 9/2009 | Boehnlein |
| 7,582,055 B2 | 9/2009 | Komiya |
| 7,582,056 B2 | 9/2009 | Noguchi |
| 7,584,534 B2 | 9/2009 | Pease |
| 7,585,274 B2 | 9/2009 | Homma |
| 7,588,535 B2 | 9/2009 | Adler |
| 7,593,051 B2 | 9/2009 | Suda |
| 7,621,868 B2 | 11/2009 | Breidenthal |
| 7,621,869 B2 | 11/2009 | Ratnakar |
| 7,623,150 B2 | 11/2009 | Kobayashi |
| 7,627,189 B2 | 12/2009 | Donomae |
| 7,630,148 B1 | 12/2009 | Yang |
| 7,671,888 B2 | 3/2010 | Nogami |
| 7,683,927 B2 | 3/2010 | Higuchi |
| 7,695,429 B2 | 4/2010 | Hino |
| 7,699,772 B2 | 4/2010 | Pauker |
| 7,701,650 B2 | 4/2010 | Lin |
| 7,725,013 B2 | 5/2010 | Sugimoto |
| 7,728,867 B2 | 6/2010 | Fukuyama |
| 7,734,160 B2 | 6/2010 | Sudo |
| 7,746,566 B2 | 6/2010 | Mizusawa |
| 7,746,572 B2 | 6/2010 | Asami |
| 7,749,156 B2 | 7/2010 | Ouchi |
| 7,749,159 B2 | 7/2010 | Crowley |
| 7,758,495 B2 | 7/2010 | Pease |
| 7,758,499 B2 | 7/2010 | Adler |
| 7,772,786 B2 | 8/2010 | Hosoda |
| 7,773,110 B2 | 8/2010 | Abe |
| 7,773,122 B2 | 8/2010 | Irion |
| 7,773,318 B2 | 8/2010 | Takato |
| 7,775,971 B2 | 8/2010 | Fujimori |
| 7,775,973 B2 | 8/2010 | Okada |
| 7,789,822 B2 | 9/2010 | Suzuki |
| 7,800,656 B2 | 9/2010 | Takeuchi |
| RE41,807 E | 10/2010 | Yokoi |
| 7,821,529 B2 | 10/2010 | Mochida |
| 7,837,614 B2 | 11/2010 | Segawa |
| 7,841,880 B2 | 11/2010 | Ikeda |
| 7,846,090 B2 | 12/2010 | Pilvisto |
| 7,852,513 B2 | 12/2010 | Donornae |
| 7,893,956 B2 | 2/2011 | Ayrenschmalz |
| 7,896,802 B2 | 3/2011 | Otawara |
| 7,901,352 B2 | 3/2011 | Minarni |
| 7,907,168 B2 | 3/2011 | Eino |
| 7,907,170 B2 | 3/2011 | Watanabe |
| 7,907,352 B2 | 3/2011 | Miyano |
| 7,914,443 B2 | 3/2011 | Uchirnura |
| 7,918,788 B2 | 4/2011 | Lin |
| 7,938,773 B2 | 5/2011 | Kawai |
| 7,940,296 B2 | 5/2011 | Ogino |
| 7,942,814 B2 | 5/2011 | Remijan |
| 7,951,068 B2 | 5/2011 | Kura |
| 7,967,745 B2 | 6/2011 | Gilad |
| 7,976,462 B2 | 7/2011 | Wright |
| 7,995,093 B2 | 8/2011 | Takeuchi |
| 7,998,064 B2 | 8/2011 | Otawara |
| 8,002,696 B2 | 8/2011 | Suzuki |
| 8,027,101 B2 | 9/2011 | Suda |
| 8,033,992 B2 | 10/2011 | Hino |
| 8,035,684 B2 | 10/2011 | Wakito |
| 8,038,600 B2 | 10/2011 | Uchiyama |
| 8,043,207 B2 | 10/2011 | Adams |
| 8,060,172 B2 | 11/2011 | Ishihara |
| 8,063,962 B2 | 11/2011 | Hagihara |
| 8,066,631 B2 | 11/2011 | Wimmer |
| 8,072,483 B2 | 12/2011 | Tomioka |
| 8,072,537 B2 | 12/2011 | Schwarz |
| 8,072,693 B2 | 12/2011 | Togino |
| 8,075,477 B2 | 12/2011 | Nakamura |
| 8,075,478 B2 | 12/2011 | Campos |
| 8,098,441 B2 | 1/2012 | Sasamoto |
| 8,100,920 B2 | 1/2012 | Gambale |
| 8,102,415 B2 | 1/2012 | Iriyama |
| 8,105,233 B2 | 1/2012 | AbouElKheir |
| 8,113,846 B2 | 2/2012 | Wallaker |
| 8,125,514 B2 | 2/2012 | Sekiguchi |
| 8,125,515 B2 | 2/2012 | Hibi |
| 8,130,454 B2 | 3/2012 | Noguchi |
| 8,135,192 B2 | 3/2012 | Matsuzaki |
| 8,135,454 B2 | 3/2012 | Daniels |
| 8,139,296 B2 | 3/2012 | Ito |
| 8,144,191 B2 | 3/2012 | Kawanishi |
| 8,149,274 B2 | 4/2012 | Yamazaki |
| 8,152,718 B2 | 4/2012 | Cheng |
| 8,152,821 B2 | 4/2012 | Gambale |
| 8,157,798 B2 | 4/2012 | Takahashi |
| 8,164,836 B2 | 4/2012 | Uzawa |
| 8,167,791 B2 | 5/2012 | Tanaka |
| 8,167,795 B2 | 5/2012 | Hoeg |
| 8,167,796 B2 | 5/2012 | Negishi |
| 8,182,419 B2 | 5/2012 | Kohno |
| 8,187,171 B2 | 5/2012 | Irion |
| 8,187,174 B2 | 5/2012 | Wang |
| 8,189,041 B2 | 5/2012 | Konishi |
| 8,189,062 B2 | 5/2012 | Irion |
| 8,194,380 B2 | 6/2012 | Murata |
| 8,197,400 B2 | 6/2012 | Boutillette |
| 8,200,042 B2 | 6/2012 | Doi |
| 8,208,015 B2 | 6/2012 | Unsai |
| 8,211,009 B2 | 7/2012 | Tanaka |
| 8,212,862 B2 | 7/2012 | Kase |
| 8,212,863 B2 | 7/2012 | Tanaka |
| 8,221,309 B2 | 7/2012 | Iida |
| 8,221,311 B2 | 7/2012 | Campos |
| 8,223,198 B2 | 7/2012 | Shibasaki |
| 8,228,369 B2 | 7/2012 | Kojima |
| 8,229,549 B2 | 7/2012 | Whitman |
| 8,235,942 B2 | 8/2012 | Frassica |
| 8,248,414 B2 | 8/2012 | Gattani |
| 8,262,558 B2 | 9/2012 | Sato |
| 8,262,565 B2 | 9/2012 | Okada |
| 8,279,275 B2 | 10/2012 | Gono |
| 8,295,566 B2 | 10/2012 | Nishimura |
| 8,300,325 B2 | 10/2012 | Katahira |
| 8,310,529 B2 | 11/2012 | Krupnick |
| 8,334,900 B2 | 12/2012 | Qu |
| 8,345,092 B2 | 1/2013 | Takasaki |
| 8,348,835 B2 | 1/2013 | Fujimori |
| 8,360,960 B2 | 1/2013 | Sasaki |
| 8,360,964 B2 | 1/2013 | Ertas |
| 8,366,623 B2 | 2/2013 | Misono |
| 8,382,673 B2 | 2/2013 | Nagano |

(56) References Cited

U.S. PATENT DOCUMENTS

| | | |
|---|---|---|
| 8,394,013 B2 | 3/2013 | Ichimura |
| 8,394,014 B2 | 3/2013 | Fuerst |
| 8,425,405 B2 | 4/2013 | Mitani |
| 8,435,173 B2 | 5/2013 | Hosaka |
| 8,439,829 B2 | 5/2013 | Miyamoto |
| 8,444,547 B2 | 5/2013 | Miyarnoto |
| 8,444,548 B2 | 5/2013 | Kumei |
| 8,449,456 B2 | 5/2013 | Ueno |
| 8,449,457 B2 | 5/2013 | Aizenfeld |
| 8,456,562 B2 | 6/2013 | Ishii |
| 8,460,182 B2 | 6/2013 | Ouyang |
| 8,465,421 B2 | 6/2013 | Finkman |
| 8,480,670 B2 | 7/2013 | Sugita |
| 8,491,467 B2 | 7/2013 | Miyamoto |
| 8,520,919 B2 | 8/2013 | Stepp |
| 8,523,764 B2 | 9/2013 | Hatcher |
| 8,523,766 B2 | 9/2013 | Kudoh |
| 8,764,642 B2 | 7/2014 | Bendele |
| 9,144,373 B2 | 9/2015 | Kaye |
| 2002/0007110 A1 | 1/2002 | Irion |
| 2002/0087047 A1 | 7/2002 | Remijan |
| 2002/0098732 A1 | 7/2002 | Shimizu |
| 2002/0109771 A1 | 8/2002 | Ledbetter |
| 2002/0109774 A1 | 8/2002 | Meron |
| 2002/0151768 A1 | 10/2002 | Akiba |
| 2002/0161281 A1 | 10/2002 | Jaffe |
| 2002/0161282 A1 | 10/2002 | Fulghum |
| 2002/0183591 A1 | 12/2002 | Matsuura |
| 2003/0030918 A1 | 2/2003 | Murayama |
| 2003/0032860 A1 | 2/2003 | Avni |
| 2003/0036681 A1 | 2/2003 | Aviv |
| 2003/0055314 A1 | 3/2003 | Petitto |
| 2003/0083552 A1 | 5/2003 | Remijan |
| 2003/0125788 A1 | 7/2003 | Long |
| 2003/0130564 A1 | 7/2003 | Martone |
| 2003/0139648 A1 | 7/2003 | Foley |
| 2003/0158462 A1 | 8/2003 | Takase |
| 2003/0181787 A1 | 9/2003 | Kondo |
| 2003/0199860 A1 | 10/2003 | Loeb |
| 2004/0015049 A1 | 1/2004 | Zaar |
| 2004/0019347 A1 | 1/2004 | Sakurai |
| 2004/0024290 A1 | 2/2004 | Root |
| 2004/0034311 A1 | 2/2004 | Mihaicik |
| 2004/0073120 A1 | 4/2004 | Motz |
| 2004/0104999 A1 | 6/2004 | Okada |
| 2004/0111012 A1 | 6/2004 | Whitman |
| 2004/0133076 A1 | 7/2004 | Kobayashi |
| 2004/0138532 A1 | 7/2004 | Glukhovsky |
| 2004/0143162 A1 | 7/2004 | Krattiger |
| 2004/0158129 A1 | 8/2004 | Okada |
| 2004/0160682 A1 | 8/2004 | Miyano |
| 2004/0176661 A1 | 9/2004 | Futatsugi |
| 2004/0190159 A1 | 9/2004 | Hasegawa |
| 2004/0210113 A1 | 10/2004 | Hasegawa |
| 2004/0220451 A1 | 11/2004 | Gravenstein |
| 2004/0242958 A1 | 12/2004 | Fujikawa |
| 2004/0242961 A1 | 12/2004 | Bughici |
| 2004/0249247 A1 | 12/2004 | Iddan |
| 2004/0254423 A1 | 12/2004 | Wendlandt |
| 2004/0260151 A1 | 12/2004 | Akiba |
| 2004/0267093 A1 | 12/2004 | Miyagi |
| 2005/0020876 A1 | 1/2005 | Shioda |
| 2005/0027164 A1 | 2/2005 | Barbato |
| 2005/0038317 A1 | 2/2005 | Ratnakar |
| 2005/0038318 A1 | 2/2005 | Goldwasser |
| 2005/0043583 A1 | 2/2005 | Killmann |
| 2005/0080342 A1 | 4/2005 | Gilreath |
| 2005/0090709 A1 | 4/2005 | Okada |
| 2005/0096501 A1 | 5/2005 | Stelzer |
| 2005/0154255 A1 | 7/2005 | Jacobs |
| 2005/0154262 A1 | 7/2005 | Banik |
| 2005/0182295 A1 | 8/2005 | Soper |
| 2005/0203338 A1 | 9/2005 | Couvillon |
| 2005/0234296 A1 | 10/2005 | Saadat |
| 2005/0234347 A1 | 10/2005 | Yamataka |
| 2005/0251127 A1 | 11/2005 | Brosch |
| 2005/0256376 A1 | 11/2005 | Bar-Or |
| 2005/0261553 A1 | 11/2005 | Swain |
| 2005/0272975 A1 | 12/2005 | McWeeney |
| 2005/0283048 A1 | 12/2005 | Gill |
| 2005/0284491 A1 | 12/2005 | Tashiro |
| 2006/0004257 A1 | 1/2006 | Gilad |
| 2006/0047184 A1 | 3/2006 | Banik |
| 2006/0052663 A1 | 3/2006 | Koitabashi |
| 2006/0063976 A1* | 3/2006 | Aizenfeld .......... A61B 1/00096 600/179 |
| 2006/0069307 A1 | 3/2006 | Boulais |
| 2006/0069314 A1 | 3/2006 | Farr |
| 2006/0149129 A1 | 7/2006 | Watts |
| 2006/0173244 A1 | 8/2006 | Boulais |
| 2006/0183971 A1 | 8/2006 | Haviv |
| 2006/0183975 A1 | 8/2006 | Saadat |
| 2006/0189845 A1 | 8/2006 | Maahs |
| 2006/0211916 A1 | 9/2006 | Kasahara |
| 2006/0217594 A1 | 9/2006 | Ferguson |
| 2006/0224040 A1 | 10/2006 | Khait |
| 2006/0229499 A1 | 10/2006 | Eisenkolb |
| 2006/0241347 A1 | 10/2006 | Whitehead |
| 2006/0252994 A1 | 11/2006 | Ratnakar |
| 2006/0264704 A1 | 11/2006 | Fujimori |
| 2006/0293556 A1 | 12/2006 | Garner |
| 2006/0293562 A1 | 12/2006 | Uchimura |
| 2007/0015964 A1 | 1/2007 | Eversull |
| 2007/0015968 A1 | 1/2007 | Shelnutt |
| 2007/0019916 A1 | 1/2007 | Takami |
| 2007/0020694 A1 | 1/2007 | Pickford |
| 2007/0030345 A1 | 2/2007 | Amling |
| 2007/0049803 A1 | 3/2007 | Moriyama |
| 2007/0055100 A1 | 3/2007 | Kato |
| 2007/0073109 A1 | 3/2007 | Irion |
| 2007/0078304 A1 | 4/2007 | Shimizu |
| 2007/0083081 A1 | 4/2007 | Schlagenhauf |
| 2007/0100206 A1 | 5/2007 | Lin |
| 2007/0106119 A1 | 5/2007 | Hirata |
| 2007/0115376 A1 | 5/2007 | Igarashi |
| 2007/0118019 A1 | 5/2007 | Mitani |
| 2007/0123748 A1 | 5/2007 | Meglan |
| 2007/0142711 A1 | 6/2007 | Bayer |
| 2007/0162095 A1 | 7/2007 | Kimmel |
| 2007/0167673 A1 | 7/2007 | Enomoto |
| 2007/0167681 A1 | 7/2007 | Gill |
| 2007/0173686 A1 | 7/2007 | Lin |
| 2007/0173687 A1 | 7/2007 | Shima |
| 2007/0177008 A1 | 8/2007 | Bayer |
| 2007/0177009 A1 | 8/2007 | Bayer |
| 2007/0182842 A1* | 8/2007 | Sonnenschein .... A61B 1/00124 348/340 |
| 2007/0185384 A1 | 8/2007 | Bayer |
| 2007/0197875 A1 | 8/2007 | Osaka |
| 2007/0203396 A1 | 8/2007 | McCutcheon |
| 2007/0206945 A1 | 9/2007 | DeLorme |
| 2007/0208225 A1 | 9/2007 | Czaniera |
| 2007/0213590 A1 | 9/2007 | Squicciarini |
| 2007/0213591 A1 | 9/2007 | Aizenfeld |
| 2007/0225556 A1 | 9/2007 | Ortiz |
| 2007/0225565 A1 | 9/2007 | Ogino |
| 2007/0229656 A1 | 10/2007 | Khait |
| 2007/0244353 A1 | 10/2007 | Larsen |
| 2007/0244362 A1 | 10/2007 | El-Hachem |
| 2007/0244366 A1 | 10/2007 | Murata |
| 2007/0246506 A1 | 10/2007 | Hamazaki |
| 2007/0249899 A1 | 10/2007 | Seifert |
| 2007/0265498 A1 | 11/2007 | Ito |
| 2007/0282165 A1 | 12/2007 | Hopkins |
| 2007/0293720 A1 | 12/2007 | Bayer |
| 2008/0009672 A1 | 1/2008 | Krattiger |
| 2008/0021274 A1 | 1/2008 | Bayer |
| 2008/0021281 A1 | 1/2008 | Fujimori |
| 2008/0039689 A1 | 2/2008 | Yoshimitsu |
| 2008/0039693 A1 | 2/2008 | Karasawa |
| 2008/0045797 A1 | 2/2008 | Yasushi |
| 2008/0051628 A1 | 2/2008 | Pecherer |
| 2008/0051629 A1 | 2/2008 | Sugiyama |
| 2008/0051655 A1 | 2/2008 | Sato |

(56) References Cited

U.S. PATENT DOCUMENTS

| | | |
|---|---|---|
| 2008/0058595 A1 | 3/2008 | Snoke |
| 2008/0058598 A1 | 3/2008 | Ries |
| 2008/0058601 A1 | 3/2008 | Fujimori |
| 2008/0064931 A1 | 3/2008 | Schena |
| 2008/0065127 A1 | 3/2008 | Adams |
| 2008/0071290 A1 | 3/2008 | Larkin |
| 2008/0100699 A1 | 5/2008 | Hibi |
| 2008/0130108 A1 | 6/2008 | Bayer |
| 2008/0139881 A1 | 6/2008 | Cover |
| 2008/0163652 A1 | 7/2008 | Shatskin |
| 2008/0167529 A1 | 7/2008 | Otawara |
| 2008/0171910 A1 | 7/2008 | Kanazawa |
| 2008/0177139 A1 | 7/2008 | Courtney |
| 2008/0177140 A1 | 7/2008 | Cline |
| 2008/0188715 A1 | 8/2008 | Fujimoto |
| 2008/0221388 A1 | 9/2008 | Seibel et al. |
| 2008/0225134 A1 | 9/2008 | Amling |
| 2008/0255425 A1 | 10/2008 | Voegele |
| 2008/0262302 A1 | 10/2008 | Azarbarzin |
| 2008/0262312 A1 | 10/2008 | Carroll |
| 2008/0312497 A1 | 12/2008 | Elmouelhi |
| 2009/0005643 A1 | 1/2009 | Smith |
| 2009/0054790 A1 | 2/2009 | Czaniera |
| 2009/0062615 A1 | 3/2009 | Yamaya |
| 2009/0086017 A1 | 4/2009 | Miyano |
| 2009/0093679 A1 | 4/2009 | Suigetsu |
| 2009/0118577 A9 | 5/2009 | Snay |
| 2009/0137869 A1 | 5/2009 | Soutorine |
| 2009/0147076 A1 | 6/2009 | Ertas |
| 2009/0161234 A1 | 6/2009 | Sasamoto |
| 2009/0163769 A1 | 6/2009 | Robertson |
| 2009/0209811 A1 | 8/2009 | Higuchi |
| 2009/0216084 A1 | 8/2009 | Yamane |
| 2009/0231419 A1 | 9/2009 | Bayer |
| 2009/0247831 A1 | 10/2009 | Miyamoto |
| 2009/0253966 A1 | 10/2009 | Ichimura |
| 2009/0259097 A1 | 10/2009 | Thompson |
| 2009/0259102 A1 | 10/2009 | Koninckx |
| 2009/0268011 A1 | 10/2009 | Scott |
| 2009/0284649 A1 | 11/2009 | Pease |
| 2009/0287047 A1 | 11/2009 | Onoda |
| 2009/0287192 A1 | 11/2009 | Vivenzio |
| 2009/0290236 A1 | 11/2009 | Wang |
| 2009/0299144 A1 | 12/2009 | Shigemori |
| 2009/0306474 A1 | 12/2009 | Wilson |
| 2009/0306476 A1 | 12/2009 | Banik |
| 2009/0318757 A1 | 12/2009 | Singh |
| 2010/0010301 A1 | 1/2010 | Hale |
| 2010/0010302 A1 | 1/2010 | Hadani |
| 2010/0013914 A1 | 1/2010 | Bettesh |
| 2010/0016673 A1 | 1/2010 | Bandy |
| 2010/0030020 A1 | 2/2010 | Sanders |
| 2010/0042097 A1 | 2/2010 | Newton |
| 2010/0047733 A1 | 2/2010 | Nahlieli |
| 2010/0053312 A1 | 3/2010 | Watanabe |
| 2010/0073470 A1 | 3/2010 | Takasaki |
| 2010/0076268 A1 | 3/2010 | Takasugi |
| 2010/0081874 A1 | 4/2010 | Miyamoto |
| 2010/0081875 A1 | 4/2010 | Fowler |
| 2010/0087706 A1 | 4/2010 | Syed |
| 2010/0121142 A1 | 5/2010 | Ouyang |
| 2010/0123950 A1 | 5/2010 | Fujiwara |
| 2010/0130822 A1 | 5/2010 | Katayama |
| 2010/0137682 A1 | 6/2010 | Doguchi |
| 2010/0137687 A1 | 6/2010 | Schwartz |
| 2010/0141746 A1 | 6/2010 | Ikeda |
| 2010/0152612 A1 | 6/2010 | Headley |
| 2010/0160729 A1 | 6/2010 | Smith |
| 2010/0174144 A1 | 7/2010 | Hsu |
| 2010/0185056 A1 | 7/2010 | Gordon |
| 2010/0187408 A1 | 7/2010 | Klem |
| 2010/0201985 A1 | 8/2010 | Wang |
| 2010/0204546 A1* | 8/2010 | Hassidov ............ A61B 1/00103 600/114 |
| 2010/0204609 A1 | 8/2010 | Worth |
| 2010/0217076 A1 | 8/2010 | Ratnakar |
| 2010/0217081 A1 | 8/2010 | Deppmeier |
| 2010/0228086 A1 | 9/2010 | Ohki |
| 2010/0245653 A1 | 9/2010 | Bodor |
| 2010/0249496 A1 | 9/2010 | Cardenas |
| 2010/0249513 A1 | 9/2010 | Tydlaska |
| 2010/0256447 A1 | 10/2010 | Dubi |
| 2010/0286475 A1 | 11/2010 | Robertson |
| 2010/0296178 A1 | 11/2010 | Genet |
| 2010/0298640 A1 | 11/2010 | Oneda |
| 2010/0298773 A1 | 11/2010 | Nitsan |
| 2010/0305503 A1 | 12/2010 | Fang |
| 2010/0313061 A1 | 12/2010 | Derrick |
| 2010/0317919 A1 | 12/2010 | Takaoka |
| 2010/0317921 A1 | 12/2010 | Marple |
| 2010/0326703 A1 | 12/2010 | Gilad |
| 2011/0028790 A1 | 2/2011 | Farr |
| 2011/0054256 A1 | 3/2011 | Cushner |
| 2011/0112363 A1 | 5/2011 | Koga |
| 2011/0160530 A1 | 6/2011 | Ratnakar |
| 2011/0169931 A1 | 7/2011 | Pascal |
| 2011/0184243 A1 | 7/2011 | Wright |
| 2011/0196200 A1 | 8/2011 | Glozman |
| 2011/0196204 A1 | 8/2011 | Setty |
| 2011/0211267 A1 | 9/2011 | Takato |
| 2011/0224487 A1 | 9/2011 | Ogawa |
| 2011/0245600 A1 | 10/2011 | Ishii |
| 2011/0245609 A1 | 10/2011 | Laser |
| 2011/0257478 A1 | 10/2011 | Kleiner |
| 2011/0263938 A1 | 10/2011 | Levy |
| 2011/0282144 A1 | 11/2011 | Gettman |
| 2011/0282148 A1 | 11/2011 | Kase |
| 2011/0288374 A1 | 11/2011 | Hadani |
| 2011/0295061 A1 | 12/2011 | Haramaty |
| 2011/0295062 A1 | 12/2011 | GratacosSolsona |
| 2011/0295064 A1 | 12/2011 | Kagawa |
| 2011/0306832 A1 | 12/2011 | Bassan |
| 2011/0313249 A1 | 12/2011 | Viola |
| 2012/0010465 A1 | 1/2012 | Erikawa |
| 2012/0029291 A1 | 2/2012 | Wallace |
| 2012/0040305 A1 | 2/2012 | Karazivan |
| 2012/0041534 A1 | 2/2012 | Clerc |
| 2012/0046524 A1 | 2/2012 | Miyamoto |
| 2012/0053407 A1 | 3/2012 | Levy |
| 2012/0057251 A1 | 3/2012 | Takato |
| 2012/0065468 A1 | 3/2012 | Levy |
| 2012/0071748 A1 | 3/2012 | Mark |
| 2012/0078042 A1 | 3/2012 | Uram |
| 2012/0088965 A1 | 4/2012 | Stokes |
| 2012/0095391 A1 | 4/2012 | Bendele |
| 2012/0104230 A1 | 5/2012 | Eismann |
| 2012/0178995 A1 | 7/2012 | Newton |
| 2012/0209062 A1 | 8/2012 | Qiao |
| 2012/0229615 A1 | 9/2012 | Kirma |
| 2012/0232340 A1 | 9/2012 | Levy |
| 2012/0232342 A1 | 9/2012 | Reydel |
| 2012/0232343 A1 | 9/2012 | Levy |
| 2012/0253121 A1 | 10/2012 | Kitano |
| 2012/0253284 A1 | 10/2012 | Nitsan |
| 2012/0259175 A1 | 10/2012 | Reydel |
| 2012/0265094 A1 | 10/2012 | Goldfarb |
| 2013/0012778 A1 | 1/2013 | Bayer |
| 2013/0012794 A1 | 1/2013 | Zeng |
| 2013/0060086 A1 | 3/2013 | Talbert |
| 2013/0109916 A1 | 5/2013 | Levy |
| 2013/0109918 A1 | 5/2013 | Pagan |
| 2013/0110003 A1 | 5/2013 | Surti |
| 2013/0131445 A1 | 5/2013 | Zerfas |
| 2013/0131447 A1 | 5/2013 | Benning |
| 2013/0131454 A1 | 5/2013 | McCormack |
| 2013/0137930 A1 | 5/2013 | Menabde |
| 2013/0172670 A1 | 7/2013 | Levy |
| 2013/0172673 A1 | 7/2013 | Kennedy |
| 2013/0172674 A1 | 7/2013 | Kennedy |
| 2013/0172677 A1 | 7/2013 | Kennedy |
| 2013/0172678 A1 | 7/2013 | Kennedy |
| 2013/0190561 A1 | 7/2013 | Oskin |
| 2013/0194404 A1 | 8/2013 | Christiansen |
| 2013/0204088 A1 | 8/2013 | Miyamoto |

(56) References Cited

U.S. PATENT DOCUMENTS

| | | | |
|---|---|---|---|
| 2013/0253272 | A1 | 9/2013 | Takahashi |
| 2013/0267778 | A1 | 10/2013 | Rehe |
| 2013/0296649 | A1 | 11/2013 | Kirma |
| 2013/0314521 | A1 | 11/2013 | Satake |
| 2013/0317295 | A1 | 11/2013 | Morse |
| 2014/0364691 | A1 | 12/2014 | Krivopisk |
| 2016/0294112 | A1* | 10/2016 | Edidin ............... H01R 13/6205 |

FOREIGN PATENT DOCUMENTS

| | | |
|---|---|---|
| CN | 1988841 | 6/2007 |
| CN | 2936129 Y | 8/2007 |
| CN | 101061940 A | 10/2007 |
| CN | 201108422 Y | 9/2008 |
| CN | 101385633 A | 3/2009 |
| CN | 101926171 | 3/2009 |
| CN | 101396258 | 4/2009 |
| CN | 102058375 A | 5/2011 |
| CN | 102058380 A | 5/2011 |
| CN | 101061940 | 6/2011 |
| CN | 201870615 U | 6/2011 |
| CN | 102469924 | 5/2012 |
| DE | 102005008153 A1 | 11/2005 |
| EP | 0029555 A2 | 6/1981 |
| EP | 543738 A1 | 5/1993 |
| EP | 730844 | 9/1996 |
| EP | 1195630 A2 | 4/2002 |
| EP | 1325458 | 7/2003 |
| EP | 1347702 A2 | 10/2003 |
| EP | 948283 B1 | 4/2004 |
| EP | 1535565 | 6/2005 |
| EP | 1073365 B1 | 7/2005 |
| EP | 1627595 A1 | 2/2006 |
| EP | 668738 B1 | 6/2006 |
| EP | 1685790 A1 | 8/2006 |
| EP | 1472972 B1 | 10/2006 |
| EP | 1790280 A1 | 5/2007 |
| EP | 1834572 A1 | 9/2007 |
| EP | 1952750 | 8/2008 |
| EP | 1977675 | 10/2008 |
| EP | 1977682 A2 | 10/2008 |
| EP | 1974000653 | 10/2008 |
| EP | 1992292 A1 | 11/2008 |
| EP | 2022389 A1 | 2/2009 |
| EP | 2144571 A2 | 1/2010 |
| EP | 2276389 A1 | 1/2011 |
| EP | 1835847 B1 | 5/2011 |
| EP | 1870014 B1 | 1/2012 |
| EP | 2501271 A1 | 9/2012 |
| EP | 2503933 A1 | 10/2012 |
| EP | 2512577 A2 | 10/2012 |
| EP | 2529660 A1 | 12/2012 |
| EP | 2596756 A1 | 5/2013 |
| EP | 2623019 A1 | 8/2013 |
| GB | 2321132 | 7/1998 |
| GB | 2352922 A | 2/2001 |
| JP | 2010279539 | 12/1920 |
| JP | S5551270 | 5/1980 |
| JP | 55078932 | 6/1980 |
| JP | 61055657 | 11/1986 |
| JP | S6296616 | 6/1987 |
| JP | 6359332 | 11/1988 |
| JP | H0253701 | 4/1990 |
| JP | H02188709 A | 7/1990 |
| JP | H03116801 | 12/1991 |
| JP | H04341232 | 11/1992 |
| JP | 5049000594 | 3/1993 |
| JP | H05309069 | 11/1993 |
| JP | 6105000800 | 4/1994 |
| JP | 7000000352 | 1/1995 |
| JP | 8122000657 | 5/1996 |
| JP | 1013007179 | 4/1998 |
| JP | 1015001113 | 6/1998 |
| JP | 11125773 | 5/1999 |
| JP | 11137512 | 5/1999 |
| JP | H11125773 | 5/1999 |
| JP | H11125773 A | 5/1999 |
| JP | 1116009340 | 6/1999 |
| JP | 1116009341 | 6/1999 |
| JP | H11253401 | 9/1999 |
| JP | 2000171727 A | 6/2000 |
| JP | 2000325306 | 11/2000 |
| JP | 2000330015 A | 11/2000 |
| JP | 2001061762 | 3/2001 |
| JP | 2001198086 | 7/2001 |
| JP | 2002000559 | 1/2002 |
| JP | 2002017667 | 1/2002 |
| JP | 2002058636 | 2/2002 |
| JP | 200265589 A | 3/2002 |
| JP | 2002065575 | 3/2002 |
| JP | 2002078675 | 3/2002 |
| JP | 2002216902 | 8/2002 |
| JP | 2002291693 | 10/2002 |
| JP | 2003038431 | 2/2003 |
| JP | 2003061900 | 3/2003 |
| JP | 2003111724 | 4/2003 |
| JP | 2003190082 | 7/2003 |
| JP | 2003220017 | 8/2003 |
| JP | 2003245247 | 9/2003 |
| JP | 2004022391 | 1/2004 |
| JP | 2004049754 | 2/2004 |
| JP | 2004049756 | 2/2004 |
| JP | 2004129834 | 4/2004 |
| JP | 2004205779 A | 7/2004 |
| JP | 2004354888 A | 12/2004 |
| JP | 2005013557 A | 1/2005 |
| JP | 2005058547 | 3/2005 |
| JP | 2005253543 | 9/2005 |
| JP | 2005323874 A | 11/2005 |
| JP | 2006003549 A | 1/2006 |
| JP | 3765500 | 2/2006 |
| JP | 2006068109 | 3/2006 |
| JP | 2006068109 A | 3/2006 |
| JP | 2006218155 | 8/2006 |
| JP | 2006280954 | 10/2006 |
| JP | 2006288758 | 10/2006 |
| JP | 2007020866 A | 2/2007 |
| JP | 2007185276 | 7/2007 |
| JP | 2008068025 | 3/2008 |
| JP | 2008118568 | 5/2008 |
| JP | 2008161569 A | 7/2008 |
| JP | 2008229204 | 10/2008 |
| JP | 2008257108 A | 10/2008 |
| JP | 2009233186 | 10/2009 |
| JP | 2009251574 | 10/2009 |
| JP | 4445647 | 4/2010 |
| JP | 2010178766 A | 8/2010 |
| WO | 9219148 A1 | 11/1992 |
| WO | 00052643 A1 | 9/2000 |
| WO | 2002045595 | 6/2002 |
| WO | 2004026125 | 4/2004 |
| WO | 2005082228 A1 | 9/2005 |
| WO | 2006073561 | 7/2006 |
| WO | 2006105932 A1 | 10/2006 |
| WO | 2007113801 A2 | 10/2007 |
| WO | 2007087421 | 11/2007 |
| WO | 2007136859 A2 | 11/2007 |
| WO | 2008012813 A1 | 1/2008 |
| WO | 200807343 | 6/2008 |
| WO | 2008093288 | 8/2008 |
| WO | 2008139770 | 11/2008 |
| WO | 2006155776 | 12/2008 |
| WO | 2008156623 | 12/2008 |
| WO | 2009009414 | 1/2009 |
| WO | 2009025843 | 2/2009 |
| WO | 2009040744 | 4/2009 |
| WO | 2009095915 | 8/2009 |
| WO | 2010021342 | 2/2010 |
| WO | 2010028612 | 3/2010 |
| WO | 2010045406 | 4/2010 |
| WO | 2010064506 | 6/2010 |
| WO | 2010066768 | 6/2010 |
| WO | 2010146587 A1 | 12/2010 |
| WO | 2011008922 | 1/2011 |

(56) References Cited

FOREIGN PATENT DOCUMENTS

| WO | 2011041724 | | 4/2011 |
|---|---|---|---|
| WO | 2011083451 | | 7/2011 |
| WO | 2011126812 | | 10/2011 |
| WO | 2012038958 | | 3/2012 |
| WO | 2013131578 | | 3/2012 |
| WO | 2012056453 | A2 | 5/2012 |
| WO | 2012077116 | | 6/2012 |
| WO | 2012077117 | A1 | 6/2012 |
| WO | 2012088201 | A2 | 6/2012 |
| WO | 2012103266 | | 8/2012 |
| WO | 2012120507 | A1 | 9/2012 |
| WO | 2012153324 | | 11/2012 |
| WO | 2013014673 | | 1/2013 |
| WO | 2013024476 | | 2/2013 |
| WO | 2013043704 | | 3/2013 |
| WO | 2013128136 | | 9/2013 |
| WO | 2013144944 | | 10/2013 |
| WO | 2014061023 | | 4/2014 |

OTHER PUBLICATIONS

Corrected European Search Opinion for EP14186113.8, dated Apr. 29, 2015.
Extended European Search Report for EP14186113.3, dated Apr. 1, 2015.
First Image of an Endo Smart Cap, made by Medivators, and obtained from http://www.bymemedical.com/prod/1451L.jpg and advertised at http://www.medivators.com/products/endoscopy-procedure-products/irrigation-tubing/endo-smartcap%C2%AE.
First Office Action for CN 2012800171292, dated Feb. 28, 2015.
First Office Action for CN 2012800368972, dated Jun. 1, 2015.
First office action for CN2011800627366, Feb. 25, 2015.
International Search Report for PCT/EP2009/066726, dated Aug. 16, 2010.
International Search Report for PCT/IL2011/000832, dated May 16, 2012.
International Search Report for PCT/IL2011/050049, dated May 15, 2012.
International Search Report for PCT/IL2011/050050, dated May 16, 2012.
International Search Report for PCT/IL2012/050037, dated Jun. 1, 2012.
International Search Report for PCT/IL2012/050274, dated Nov. 15, 2012.
International Search Report for PCT/IL2012/050299, dated Nov. 15, 2012.
International Search Report for PCT/IL2013/050840, dated Feb. 2, 2014.
International Search Report of PCT/IL2011/000745, dated May 8, 2012.
Notice of Allowance dated Jun. 17, 2015 for U.S. Appl. No. 13/190,968.
Notice of Allowance dated Jun. 8, 2015 for U.S. Appl. No. 13/413,252.
Notice of Allowance dated Jun. 8, 2015 for U.S. Appl. No. 13/984,028.
Office Action dated Aug. 19, 2015 for U.S. Appl. No. 13/713,466.
Office Action dated Aug. 19, 2015 for U.S. Appl. No. 13/713,449.
Office Action dated Aug. 27, 2015 for U.S. Appl. No. 13/655,120.
Office Action dated Aug. 4, 2015 for U.S. Appl. No. 13/557,114.
Office Action dated Aug. 5, 2015 for U.S. Appl. No. 13/212,627.
Office Action dated Aug. 6, 2015 for U.S. Appl. No. 13/119,032.
Office Action dated Feb. 13, 2015 for U.S. Appl. No. 13/713,449.
Office Action dated Feb. 17, 2015 for U.S. Appl. No. 13/882,004.
Office Action dated Jan. 15, 2015 for U.S. Appl. No. 13/190,968.
Office Action dated Jul. 21, 2015 for U.S. Appl. No. 13/992,021.
Office Action dated Jun. 3, 2015 for U.S. Appl. No. 13/992,014.
Office Action dated Mar. 12, 2015 for U.S. Appl. No. 13/822,908.
Office Action dated Mar. 23, 2016 for U.S. Appl. No. 13/713,449.
Office Action dated Mar. 6, 2015 for U.S. Appl. No. 13/413,059.
Office Action dated May 1, 2015 for U.S. Appl. No. 13/992,021.
Office Action dated Nov. 26, 2014 for U.S. Appl. No. 13/713,466.
Office Action for Chinese Patent Application No. 201180067259.2, dated May 29, 2015.
Prosecution File History for U.S. Appl. No. 13/190,968, Jul. 26, 2011 through Jun. 17, 2015.
Supplementary European Search Report for European Application No. EP12823972, dated May 13, 2015.
Extended European Search Report for EP11847191.1, dated Jan. 15, 2016.
Examination Report for Canadian Patent Application No. CA2765559, dated Jan. 18, 2016.
Examination Search Report for Canadian Patent Application No. CA2765559, Jan. 18, 2016.
Extended European Search Report for EP11846069.0, dated Apr. 24, 2014.
Extended European Search Report for EP12817452.1, dated Mar. 9, 2015.
First Office Action for Chinese Patent Applicatio No. CN201380053351.2, dated Mar. 2, 2016.
Notice of Allowance dated Dec. 15, 2014, for U.S. Appl. No. 13/713,466.
Notice of Allowance dated Dec. 15, 2015 for U.S. Appl. No. 13/713,466.
Notice of Allowance dated Dec. 23, 2015 for U.S. Appl. No. 13/992,021.
Office Action dated Dec. 4, 2015 for U.S. Appl. No. 13/822,908.
Office Action dated Jan. 12, 2016 for U.S. Appl. No. 13/713,466.
Office Action dated Mar. 24, 2016 for U.S. Appl. No. 13/212,627.
Office Action dated Mar. 28, 2016 for U.S. Appl. No. 13/119,032.
Office Action dated Nov. 16, 2015 for U.S. Appl. No. 13/557,114.
Office Action dated Nov. 24, 2015 for U.S. Appl. No. 13/413,059.
Office Action dated Nov. 3, 2015 for U.S. Appl. No. 13/992,014.
Office Action dated Oct. 7, 2015 for U.S. Appl. No. 13/882,004.
Office Action for Chinese Patent Application No. 201280038808.8, dated May 20, 2015.
Office Action for Japanese Patent Application No. JP2014-522214, dated Apr. 26, 2016.
Office Action for Japanese Patent Application No. JP2014-525562, dated Apr. 26, 2016.
Office Action for Japanese Patent Application No. 2013-535586, dated Sep. 24, 2015
Office Action for Japanese Patent Application No. 2013-542668, dated Oct. 1, 2015.
Second image of an Endo Smart Cap, made by Medivators, and obtained from http://www.bymemedical.com/prod/150L.jpg and advertised at http://www.medivators.com/products/endoscopy-procedure-products/irrigation-tubing/endo-smartcap%C2%AE.
Second Office Action for Chinese Patent Applicatio No. CN201280038808.8, dated Feb. 25, 2016.
Second office action for Chinese Patent Application No. 201180062736.6, dated Oct. 12, 2015
Supplementary European Search Report for EP118471911, dated Jan. 16, 2015.
Office Action dated Oct. 7, 2016 for U.S. Appl. No. 13/713,449.
Notice of Allowance dated Apr. 18, 2017 for U.S. Appl. No. 13/713,449.
Office Action dated Jun. 30, 2016 for U.S. Appl. No. 13/655,120.
Second Office Action for Chinese Patent Application No. 201180067259.2, dated Mar. 30, 2016.
Extended European Search Report for application No. EP12755186, dated May 23, 2016.
Supplementary European Search Report for EP13847671, dated May 19, 2016.
Office Action dated Apr. 28, 2016 for U.S. Appl. No. 13/992,014.
Notice of Allowance dated Aug. 26, 2016 for U.S. Appl. No. 13/212,627.
Office Action dated Sep. 16, 2016 for U.S. Appl. No. 13/992,014.
Notice of Allowance dated Oct. 12, 2016 for U.S. Appl. No. 13/119,032.
Notice of Allowance dated Nov. 9, 2016 for U.S. Appl. No. 13/557,114.
Third Office Action for Chinese Patent Application No. 201180067259.2, dated Oct. 21, 2016.

(56) References Cited

OTHER PUBLICATIONS

Office Action for Chinese Patent Application No. 201180062736.6, dated Dec. 23, 2016.
Office Action for Japanese Patent Application No. 2016-105009, dated Jan. 16, 2017.
Office Action for Chinese Patent Application No. 201380053351.2, dated Dec. 13, 2016.
First Office Action for EP11847191.1, dated Feb. 21, 2017.
Office Action dated Mar. 21, 2017 for U.S. Appl. No. 13/992,014.
Examination Report for EP11846069.0, dated Feb. 21, 2017.
Extended European Search Report for EP11826512.3, dated Apr. 6, 2017.
International Search Report of PCT/IL10/00476 dated Sep. 27, 2010, 2 pages.
Office Action dated May 23, 2017 for U.S. Appl. No. 13/655,120.

\* cited by examiner

REMOVABLE TIP ENDOSCOPE

CROSS-REFERENCE TO RELATED APPLICATIONS

This application claims the benefit of U.S. Provisional Application No. 61/569,796, filed Dec. 13, 2011, the content of which is expressly incorporated herein by reference in its entirety.

FIELD OF THE INVENTION

Embodiments of the disclosure relate to a multi camera endoscope with a removable tip section.

BACKGROUND OF THE INVENTION

Endoscopes have attained great acceptance within the medical community, since they provide a means for performing procedures with minimal patient trauma, while enabling the physician to view the internal anatomy of the patient. Over the years, numerous endoscopes have been developed and categorized according to specific applications, such as cystoscopy, colonoscopy, laparoscopy, upper GI endoscopy and others.

Endoscopes may be inserted into the body's natural orifices or through an incision in the skin.

An endoscope is usually an elongated tubular shaft, rigid or flexible, having one or more video cameras or fiber optic lens assemblies at its distal end, or one or more video cameras or fiber optic lens assemblies positioned further back, e.g., more proximally on or near the lateral surface area of the tip section, and point sideways. The shaft is connected to a handle, which sometimes includes an ocular for direct viewing. Viewing is also usually possible via an external screen. Various surgical tools may be inserted through a working channel in the endoscope for performing different surgical procedures.

Among the disadvantages of existing endoscopes, are their limited field of view and their complicated packing of all the required elements, such as electronics and together with fluid carrying elements in the small sized endoscope tip section. In addition, different procedures (for example for different conditions or subjects) may require different endoscope structures and functions.

There is thus a need in the art for endoscopes, such as colonoscopies, that allow a broader field of view and also enable the function of all necessary elements in the tip section.

The foregoing examples of the related art and limitations related therewith are intended to be illustrative and not exclusive. Other limitations of the related art will become apparent to those of skill in the art upon a reading of the specification and a study of the figures.

SUMMARY OF THE INVENTION

One aspect of the disclosure relates to an endoscope comprising an elongated shaft terminating with a tip section, wherein said tip section comprises: a permanent section connected to the elongated shaft; and a removable section securely connectable to the permanent section, wherein the removable section comprises one or more capture devices and one or more light sources. In some embodiments of the endoscope, the capture device within the removable section comprises a front-facing camera. In some embodiments of the endoscope, the capture device within the removable section comprises a side-facing camera. In some embodiments of the endoscope, the capture device within the removable section comprises a front-facing camera and a side-facing camera. In some embodiments of the endoscope, the permanent section comprises one or more capture devices. In some embodiments, the capture device within the permanent section comprises a side-facing camera. In some embodiments of the endoscope, the tip section comprises a distal face and the permanent section forms a part of the distal face, and the removable section forms another part of the distal face. In some embodiments of the endoscope, the tip section comprises a distal face, and the distal face is fully comprised in the removable section. In some embodiments of the endoscope, the permanent section comprises a hollow elongated section protruding from the permanent section and the removable section comprises a channel configured to continue said hollow elongated section, so as to provide a working channel configured for insertion of a surgical tool. In some embodiments of the endoscope, the removable section comprises a hollow elongated section protruding from the removable section and the permanent section comprises a channel configured to continue said hollow elongated section, so as to provide a working channel configured for insertion of a surgical tool. In some embodiments of the endoscope, the removable section comprises an elongated section configured to pass a cable for electric or data signals, the elongated section ending with a first connector, and the permanent section comprises a recess configured to pass electric and/or data signals, said recess comprising a second connector connectable to the first connector. In some embodiments of the endoscope, the removable section comprises a first optic fiber and a first lens, and the permanent section comprises a second optic fiber and a second lens, such that the first lens corresponds to the second lens so as to transfer light between the first optic fiber and the second optic fiber. In some embodiments of the endoscope, the permanent section comprises an elongated section configured to pass a cable for electric or data signals, the elongated section ending with a first connector, and the removable section comprises a recess configured to pass electric or data signals, the recess comprising a second connector connectable to the first connector. In some embodiments of the endoscope, the endoscope further comprises a switch on the permanent section such that the endoscope can operate only if the switch is pressed by the removable section. In some embodiments of the endoscope, an indication of a status of the switch is displayed on a display device.

Another aspect of the disclosure relates to a removable section of an endoscope tip, the removable section comprising one or more capture devices and one or more light sources, wherein the removable section is connectable to a permanent section of the endoscope tip. In some embodiments of the removable section, the capture device within the removable section comprises a front-facing capture device. In some embodiments of the removable section, the capture device within the removable section comprises a side-facing camera. In some embodiments of the removable section, the capture device within the removable section comprises a front-facing camera and a side-facing camera. In some embodiments, the removable section is configured to form a part of a distal face of the endoscope tip. In some embodiments, the removable section is configured to form a full distal face of the endoscope tip. In some embodiments, the removable section comprises a channel into which a hollow elongated section protruding from the permanent section is configured to be inserted, so as to provide a working channel configured for insertion of a surgical tool. In some embodiments the removable section comprises a hollow elongated section protruding from the removable section, the hollow elongated section is configured to be inserted into a channel in the permanent section, so as to provide a working channel configured for insertion of a surgical tool. In some embodiments, the removable section comprises an elongated section configured to pass a cable for electric or data signals, the elongated section ending with a first connector, connectable to a second connector comprised in a recess in the permanent section. In some embodiments, the removable section comprises a recess configured to pass a cable for electric or data signals, the recess comprising a connector, said connector connectable to a second connector located in an elongated section protruding from the permanent section. In some embodiments, the removable section is adapted to press a switch on the permanent section such that the endoscope can operate only if the switch is pressed by the removable section. In some embodiments the removable section is configured for a single use.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Figure 1:
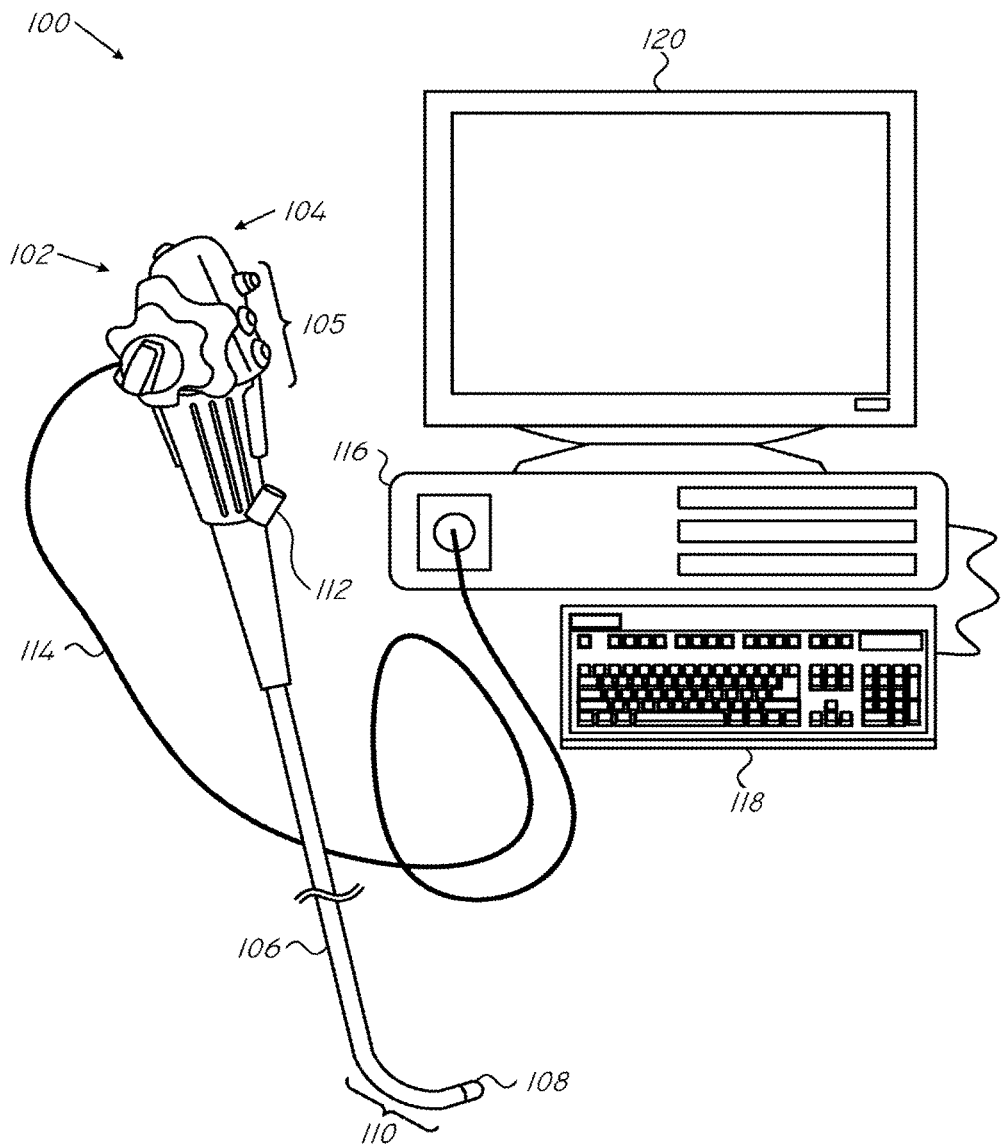
FIG. 1 shows a semi-pictorial view of an endoscopy system.

An aspect of some embodiments relates to an endoscope having a removable multi camera tip section.

The endoscope may comprise a front-pointing camera, fiber optic lens assembly, or another capturing device for capturing the area of interest, and optionally one or more light sources such as a Light Emitting Diode (LED), or one or more fluid injectors, positioned at a distal end of the endoscope for enabling the capturing device to capture images of the body cavity into which the endoscope is inserted. The endoscope may further comprise an opening at its distal end, the opening connected to a working channel, through which an operator may insert a surgical tool in order to remove, treat and/or extract a sample of the findings in the body cavity. In some embodiments, the endoscope may comprise one or more side-pointing capturing devices, and optionally additional light sources or fluid injectors, positioned further back, e.g., more proximally on the endoscope, on or near the lateral surface area of the tip section.

An endoscope is a general term for a wide variety of devices, which are adapted to be used in a variety of applications, such as cystoscopy, colonoscopy, laparoscopy, upper GI endoscopy or others.

According to some embodiments, one technical problem addressed by the disclosed apparatus and method relates to multiple endoscope configurations being required for handling the multiplicity of applications. Different configurations may require different type, number, positioning, directing, focusing or other tuning of the capturing devices, light sources or other components on the endoscope. Therefore, although multiple parts of an endoscope system may be common to many of the configurations, yet multiple endoscopes may be required. This poses significant requirements on a health institute, including for example financial requirements, storage, maintenance, training or the like.

Some different configurations may also be required for different patients or patient types, such as adults, children, babies, or the like.

Some different configurations may also be required for different procedures, such as Colonoscopy, Gastroscopy, Endoscopic Ultrasound (EUS), ERCP or the like.

Yet another technical problem addressed by embodiments of the disclosure relates to maintenance costs. When replacing the camera head, for example due to defective objective lens, the entire colonoscope has to be disassembled, which is an expensive process.

According to some embodiments, a technical solution may be the provisioning of an endoscope having a removable tip section. The tip section may also be partially removable, for example, with a permanent section and a removable section. The removable section of the tip may be removably connected or attached to the permanent section of the tip which is connected to the shaft, so that endoscopes having different configurations can be used with the same system. According to the endoscopic task to be performed, a removable section having an appropriate configuration is selected and connected to the shaft or to the permanent section. When the endoscopy session is over, the removable section of the tip may be removed and another removable section having the same or a different configuration can be connected to the permanent section or to the shaft.

In some embodiments, the removable section of the tip comprises a substantially full cross section of the tip, for example the whole distal surface of the tip, possibly excluding some openings or small parts such as rings. In some of these embodiments, all channels and flows going through the tip, such as optic fibers, power supply, water supply, data lines transferring images, working channels for transferring equipment, or the like, are made of at least two parts which may be connected when the removable section is attached to the permanent section. However, in other embodiments of the full cross section removable sections, there may still be some materials or equipment which make their way only through the permanent section, which has one or more protruding parts going into and through the removable section.

In other embodiments, all cross sections of the removable section are substantially partial to the cross sections of the tip, such that at least one of the channels going through the tip are not split and are fully contained within the permanent section.

It will be appreciated that when the removable section is attached to the permanent section, all channels and flows which are split between the permanent section and the removable section, are securely connected such that no tool, material or energy may leak between the parts, and that all data may be continuously transferred.

In some embodiments, the removable section may be attached to the permanent section in a secure manner which will ensure that the removable section will not mistakenly disconnect from the permanent section within the body. A verification mechanism may be provided which adds extra security measures.

One technical effect of embodiments of the disclosed subject matter relates to providing an endoscope with removable tip section. This enables the medical stuff to replace the tip section of the endoscope in accordance with the required functionality, so as to use for each type of endoscopic session the most suitable endoscope configuration, equipment, size, or the like. Different removable sections may then be used according to varying needs, thus eliminating the need for purchasing and maintaining multiple endoscopes for different applications. Thus, different removable sections may be of different configurations, for example have the image capturing components, light sources, or working channels located at different locations on the removable section, thus adjusting to the specific body cavity explored or to possible findings within the body cavity. In other embodiments, the relative location between the image capturing components and the light sources may differ. In yet other embodiments, different removable sections may contain different types of cameras, differing for example in their wave length, lens assembly, sensor or other parts, pointing directions, field of view, or other parameters. The light sources may also differ between different configurations, in order to provide the type of light which the used sensor is sensitive to. Different removable sections can be made to adjust to different patients, for example removable sections can be manufactured in different sizes for adults, children or babies. Different removable sections can also be used when different view fields, different viewing angles or different optical characteristics are required, for example in some situations a viewing angle of 170° may be used, while in situations that require viewing more details of a smaller area a viewing angle of 140° can be used.

Another technical effect of relates to providing a disposable removable section, thus eliminating the need for sterilization or reprocessing and reducing contamination risks.

Yet another technical effect of the disclosed subject matter, according to some embodiments, relates to providing a removable section which can be made personalized in order to provide good results for a particular patient.

Yet another technical effect of the disclosed subject matter, according to some embodiments, relates to the replaceable top enabling a health care facility to maintain only a small number of endoscope systems, thus reducing cost and maintenance, while using the most appropriate endoscope for each type of endoscopic session, each patient, or the like.

Referring now to FIG. 1, showing a semi-pictorial view of an endoscopy system 100. System 100 may include a removable tip endoscope 102, such as the removable tip endoscope of FIGS. 3 and/or 4. Removable tip endoscope 102 may include a handle 104, from which an elongated shaft 106 emerges. Elongated shaft 106 terminates with a tip section 108 which may be turnable by way of a bending section 110. Handle 104 may be used for maneuvering elongated shaft 106 within a body cavity; the handle may include one or more knobs and/or switches 105 which control bending section 110 as well as endoscopic functions such as fluid injection and suction. Handle 104 may further include one or more working channel openings such as working channel opening 112 through which surgical tools may be inserted.

A utility tube 114 may connect between handle 104 and a controller 116. Utility tube 114 may include therein one or more fluid channels and one or more electrical channels. The electrical channel(s) may include at least one data cable for receiving visual signals such as video signals from the camera or cameras on removable tip 102, as well as at least one power cable for providing electrical power to the cameras and to the discrete illuminators.

Controller 116 may govern power transmission to removable tip section 108 of endoscope 102, such as for the tip section's cameras and illuminators. Controller 116 may further control one or more fluid, liquid and/or suction pump which supply corresponding functionalities to endoscope 102. One or more input devices, such as a keyboard 118 may be connected to controller 116 for the purpose of human interaction with the controller. In another configuration (not shown), an input device, such as a keyboard, may be integrated with the controller in a same casing.

A display 120 may be connected to controller 116, and configured to display images and/or video streams received from the cameras of removable tip endoscope 102. Display 120 may further be operative to display a user interface for allowing a human operator to set various features of system 100.

Optionally, the image streams received from the one or more cameras of removable tip endoscope 102 may be displayed on display 120. If removable tip endoscope 102 comprises multiple cameras, the images may be displayed on display 120 side-by-side, interchangeably (namely, the operator may switch between views from the different cameras manually), or in any other manner. Alternatively, the video streams may be processed by controller 116 to combine them into a single video frame which may be panoramic or three-dimensional, based on an overlap between fields of view of the cameras or on known coordinates obtained for example from fiducials.

In another configuration (not shown), two or more displays may be connected to controller 116, each for displaying a video stream from a different camera of the multi-camera endoscope.

Figure 2:
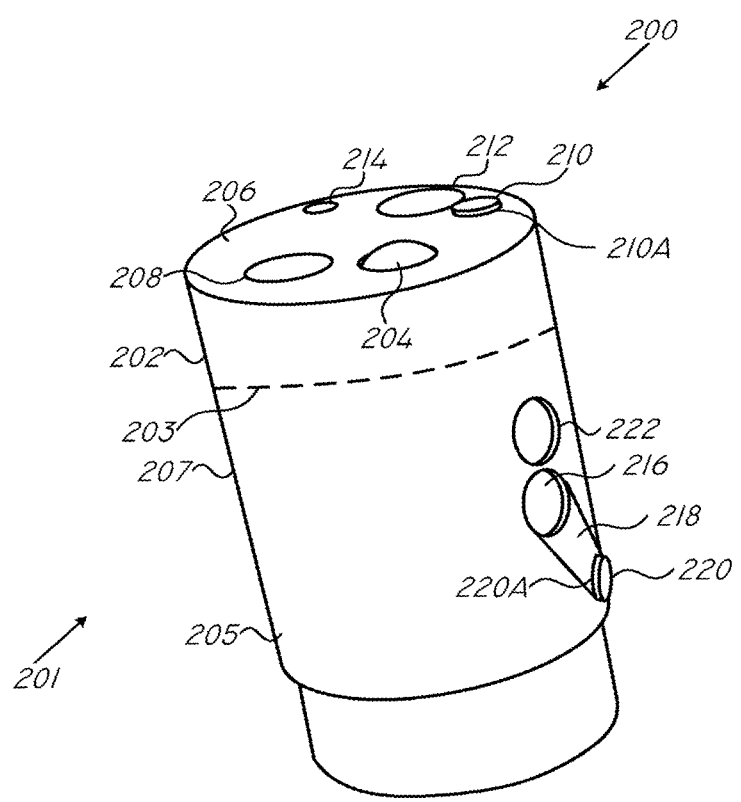
FIG. 2 shows a perspective view of a multi-camera endoscope.

Referring now to FIG. 2, showing a perspective view of a removable tip endoscope.

Endoscope 200 may include an elongated shaft (not shown), a bending section (not shown) and a tip section 201 which terminates the endoscope. The bending section may enable the turning of tip section 201 in different directions. Tip section 201 may comprise a removable section 202 and a permanent section 207 connected along line 203.

Removable section 202 may include therein a front-pointing capturing device such as a camera or a video camera 204 which may capture images through a hole in a distal end surface 206 of tip section 201. A discrete front illuminator 208, which is optionally a light-emitting diode (LED), may be associated with front-pointing camera 204 and used for illuminating its field of view through another hole in distal end surface 206. The LED may be a white light LED, an infrared light LED, a near infrared light LED or an ultraviolet light LED. The light may be generated internally within endoscope tip section 201, or generated remotely and transferred, for example, by a fiber optic. In some embodiments, removable section 202 may comprise two or more illuminators, wherein at least one may generate the light internally, and at least one may provide remotely generated light.

A front fluid injector 210 may be used for cleaning at least one of front-pointing camera 204 and discrete front illuminator 208. Front fluid injector 210 may be slightly elevated from distal end surface 206, to enable it to inject fluid, from its side 210a, onto front-pointing camera 204 and discrete front illuminator 208. Front fluid injector 210 may be configured to inject fluids such as water, air and/or the like.

Distal end surface 206 may further include a hole defining a working channel 212. Working channel 212 may be a hollow tube configured for insertion of a surgical tool to operate on various tissues. For example, miniature forceps may be inserted through working channel 212 in order to remove a polyp or sample of which for biopsy. In alternative embodiments working channel 212 can be used for applying suction for evacuating various liquids and/or solids which exist in the body cavity and interfere with the inspection. In some embodiments, opening 212 can extend to an internal cylinder which comprises a part of permanent section 207.

A pathway fluid injector 214, defined by another hole in distal end surface 206, may be used for inflating and/or cleaning the body cavity into which endoscope 200 is inserted. Inflation may be performed by flowing air or another gas through pathway fluid injector 214, and may be beneficial for cases in which the body cavity, such as the colon, is shriveled or otherwise does not allow for efficient inspection. Cleaning may be achieved, for example, by injecting a liquid, such as water or saline, on an unclean area of the body cavity Furthermore, pathway fluid injector 214 (or a different tube, not shown) may be used for applying suction, in order to evacuate various liquids and/or solids which exist in the body cavity and interfere with the inspection.

Permanent section 207 of tip section 201 may include therein a side-pointing camera 216 which may capture images through a hole in a cylindrical surface 205 of the permanent section 207 of tip section 201. A side illuminator 222, which is optionally similar to front illuminator 208, may be associated with side-pointing camera 216 and used for illuminating its field of view through another hole in cylindrical surface 205. A side fluid injector 220 may be used for cleaning at least one of side-pointing camera 216 and discrete side illuminator 222. In order to prevent tissue damage when cylindrical surface 205 of permanent section 207 contacts a side wall of the body cavity, side fluid injector 220 and side-pointing camera 216 may be located in a notch 218 in the cylindrical surface. This way, side fluid injector 220 may be elevated from depression 218 but still not significantly protrude from the level of cylindrical surface 205. The elevation of side fluid injector 220 may enable it to inject fluid, from its opening 220a, onto side-pointing camera 216. In an alternative configuration (not shown), one or more discrete side illuminators may also be included in the depression, so that fluid injected from the side fluid injector may reach them. In yet another configuration (not shown), a side-pointing camera, one or more side illuminators and a side fluid injector may not be located in a depression, but rather be on essentially the same level as the cylindrical surface of the tip section.

It will be appreciated that the division of tip section 201 into removable section 202 and permanent section 207 shown in FIG. 2 is schematic only and is intended as a general demonstration. The cameras, working channels, illumination channels, fluid injectors and other components may be split between removable section 202 and permanent section 207 in any other manner as demonstrated in the exemplary embodiments detailed in association with FIG. 3 to FIG. 6 below.

It will be appreciated that further flexibility may be provided if any of the capture devices (such as cameras), working channels, illumination channels and other components are provided on the removable section rather than on the permanent section. In such arrangement, each removable section is configured and equipped with the camera types and other equipment and arrangement which are most appropriate for the task. However, some equipment such as cameras of higher quality and price may be located on the permanent section, so as to better utilize such resources in multiple application types.

Figure 3:
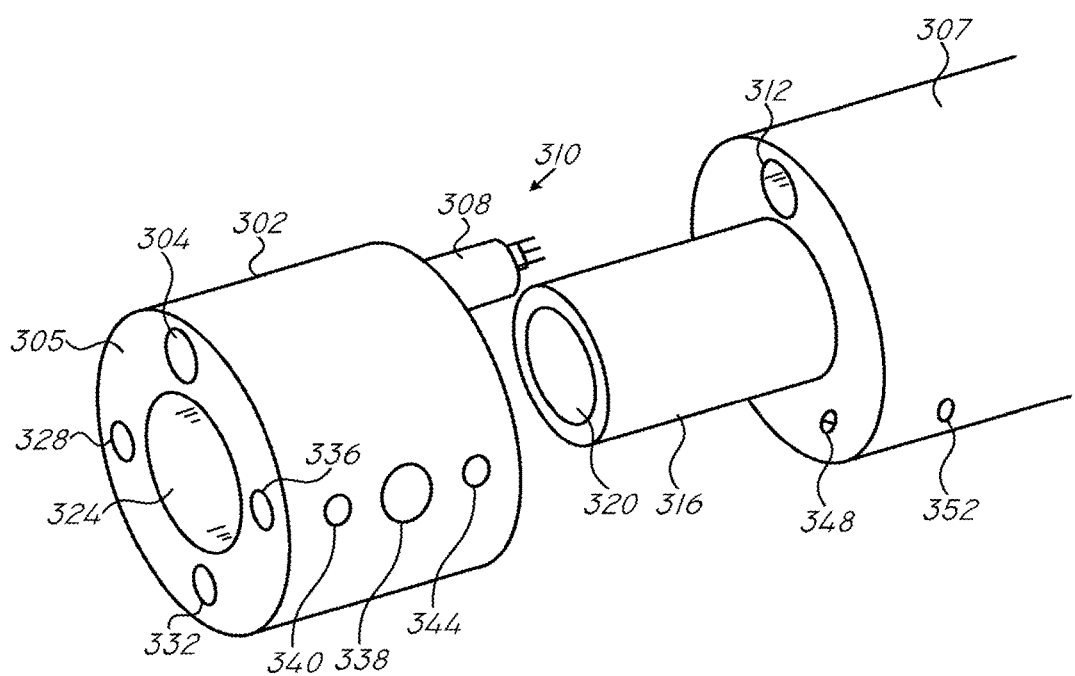
FIG. 3 shows a perspective view of a full cross section removable tip section removed from the permanent section, in accordance with some exemplary embodiments of the disclosure.

Referring now to FIG. 3, showing a perspective view of a substantially full cross section of a removable tip, removed from the permanent section.

Removable section 302 of a tip of an endoscope is shown removed from permanent section 307, wherein permanent section 307 is connected to a shaft (not shown).

Removable section 302 may comprise one or more capture devices for example video camera 304, one or more light sources such as light source 328, or one or more fluid injector such as 332 or 336.

One or more cables providing power to camera 304 and transferring images from camera 304 to the shaft go through removable section 302, into and through an elongated section 308 protruding from removable section 302. When removable section 302 is connected to permanent section 307, elongated section 308 enters a corresponding recess 312 in permanent section 307. In some embodiments, elongated section 308 may end with a connector, wherein recess 312 contains a corresponding connector, such that when elongated section 308 is entered into recess 312 the two connectors connect such that power or data can flow between the endoscope and camera 304. For example, a plug located at the end of elongated section 308 may enter a corresponding socket inside recess 312. In alternative embodiments, recess 312 may comprise a plug and elongated section 308 may comprise a socket.

Thus, electric signals or data may pass through elongated section 308 and recess 312 from the shaft to the camera.

In some embodiments, elongated section 308 may protrude from permanent section 307 while recess 312 may be placed on removable section 302.

It will be appreciated that removable section 302 or permanent section 307 may comprise additional one or more pairs of protruding sections and corresponding channels, for transferring water or other fluids or liquids, optic fibers or any other material or equipment. When the protruding sections and corresponding channels are used for transferring fluids or liquids, one or two of them may be constructed with gaskets for sealing the fluids or liquids and avoiding leakage into the body or into other parts of the endoscope tip, from a gap between removable section 302 and permanent section 307.

Permanent section 307 may also comprise a hollow elongated section 316 protruding therefrom containing channel 320. When removable section 302 is connected to permanent section 307, hollow elongated section 316 is inserted into a corresponding channel 324 in removable section 202, which extends through the entire length of removable section 302, thus enabling a surgical tool (not shown) to pass through a working channel extending from the shaft through channel 320 of hollow elongated section 316 and through channel 324 in removable section 302 to distal surface 305 of removable section 302, so that the surgical tool can be used for operating on the body cavity of the patient.

Removable section 302 may also comprise one or more side-pointing capturing devices such as camera 338, one or more light sources 340 or one or more fluid injectors 344. The utilities to camera 338, light source 340 or injector 344, may be received from the same provisioning as the front facing camera, light sources and injectors, through corresponding pipes within the body of removable section 302 around channel 324. The images captured by camera 338 may also be transferred through the same channels.

It will be appreciated that removable section 302 or permanent section 307 may comprise additional side pointing cameras, light sources or injectors.

Removable section 302 and permanent section 307 may be connected by any known mechanism, such as locking mechanism, fastening mechanism, snap mechanism, or the like.

Removable section 302 or permanent section 307 may be equipped with a button 352 for releasing the connection. In order to avoid harming the body cavity of the user, button 352 may be placed within a recess so as not to protrude from the surface of the tip section. In some embodiments, the connection may only be released if a corresponding command is provided from an external source, such as simultaneous clicking on a control on display 120 which may be translated to an electrical or mechanical effect required for releasing the connection, in order to prevent unwanted accidental release.

In some embodiments, permanent section 307 may comprise a button or another sensitive area such as switch 348 which may be touched or pressed by removable section 302, only when removable section 302 is securely connected to permanent section 307. Such button may also be electrically connected to the endoscope handle or controller and may provide an indication to the endoscope operator whether the parts are securely connected. The indication may be visual, such as an icon on display 120. In some embodiments, when the connection is released, a vocal indication may also be provided as well to alert the operator.

In some embodiments, there may be two degrees or two mechanisms of connection between removable section 302 and permanent section 307. If one degree or one mechanism is released while the endoscope is being used, the operator may receive a first alert so he or she can remove the endoscope or otherwise correct the situation before the removable section is released within the body cavity of the patient.

It will be appreciated by a person skilled in the art that if the endoscope comprises an optic fiber, then each of removable section 302 and permanent section 307 may comprise a part of the fiber, wherein the sections may comprise corresponding lenses for providing continuity between the fiber parts by transferring light.

Figure 4:
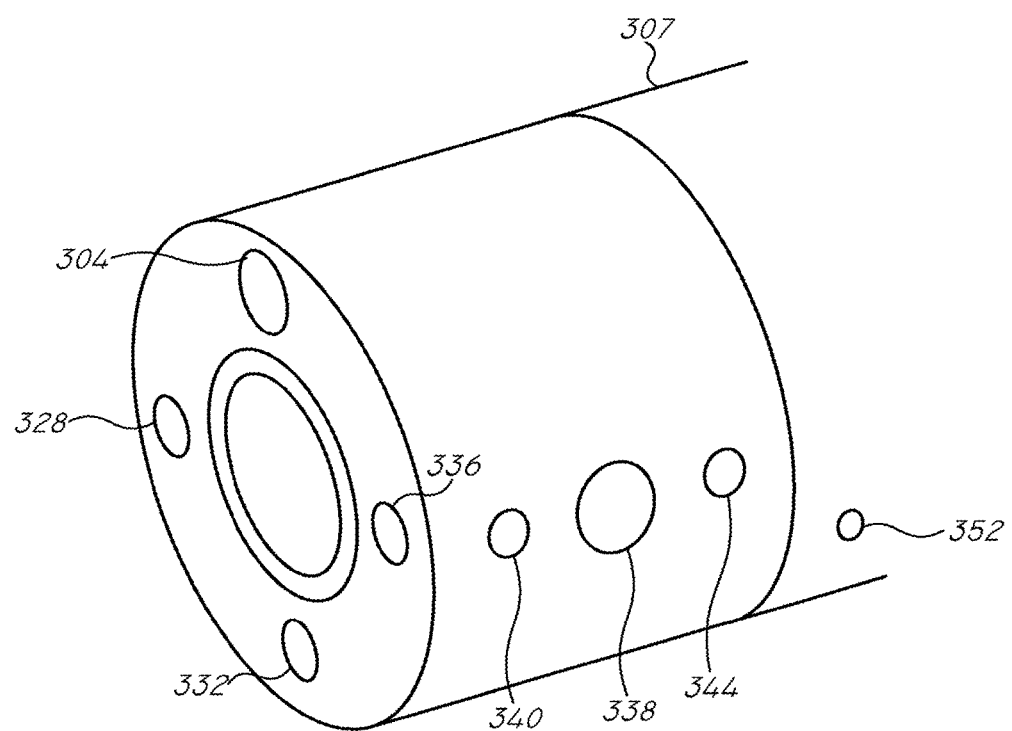
FIG. 4 shows a perspective view of a full cross section removable tip section attached to the permanent section, in accordance with some exemplary embodiments of the disclosure.

Referring now to FIG. 4 showing a perspective view of a substantially full cross section removable tip section attached to the permanent section.

In FIG. 4, removable section 302 is fully connected to permanent section 307, such that elongated section 308 and hollow elongated section 316 of FIG. 3 are inserted into corresponding recess 312 and channel 324, respectively. Electric signals or energy as well as water or fluids may pass through permanent section 307 to removable section 302, and images captured by the cameras are transferred back and may be displayed to an operator.

Figure 5:
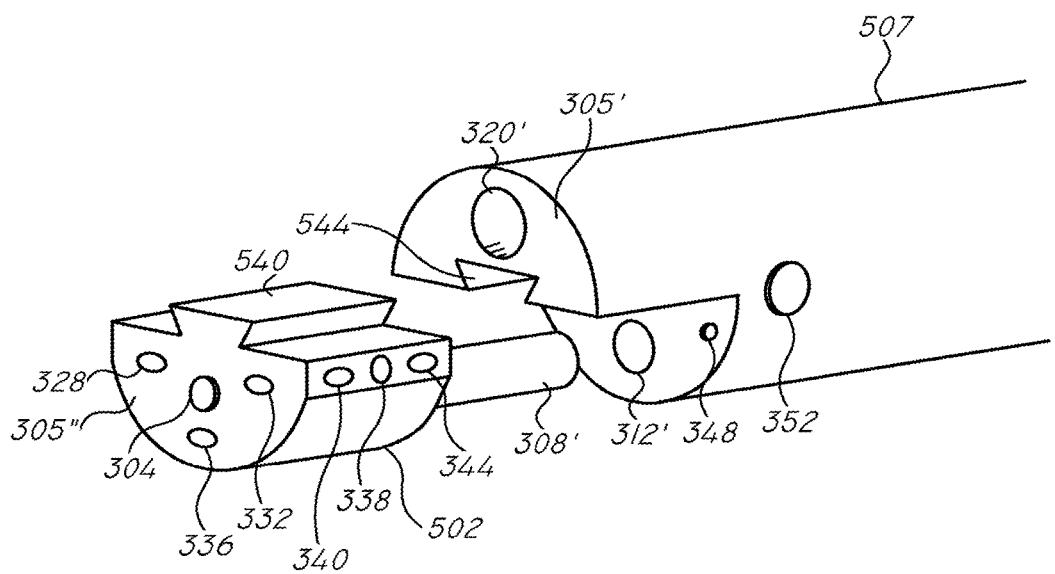
FIG. 5 shows a perspective view of a partial cross section removable tip section removed from the permanent section, in accordance with some exemplary embodiments of the disclosure.

Referring now to FIG. 5 showing a perspective view of a partial cross section removable tip section.

In FIG. 5, distal face 305 of the endoscope tip is comprised of two parts, wherein a first part 305' of distal face is of permanent section 507, while the other part 305" is of removable section 502. Thus, each cross section of removable section 502 comprises a partial cross section of the tip section when assembled of the two sections. In the exemplary embodiment of FIG. 5, channel 320' fully contained within permanent section 507 forms a working channel and reaches through permanent section 507 to the distal face so that tools or other equipment can be passed.

Removable section 502 may be equipped with cameras 304 or 338, light sources 328 or 340, or one or more fluid injector 332, 336 or 344 which may be located at the front face or on side face of removable section 502 as required. The cameras, light sources or fluid injectors may be implemented and receive utilities as detailed in association with FIG. 3 above.

Removable section 502 may also comprise one or more elongated sections such as elongated section 308' which fits into recess 312' of permanent section 507. The one or more elongated sections such as elongated section 308' may function as anchoring mechanism to secure removable section 502 within permanent section 507. Alternatively or additionally, the one or more elongated sections such as elongated section 308' may be used for transferring electric energy, fluids, liquids, optic fibers or other equipment or materials between removable section 502 and/or surface 305" and the endoscope handle and/or console.

In order to provide for full and tight connection between removable section 502 and permanent section 507, removable section 502 may comprise a trapeze shaped bulge which fits into recess 544 of permanent section 507. In alternative embodiments, removable section 502 may comprise a recess and permanent section 507 may comprise a bulge.

Permanent section 507 and removable section 502 may be connected in any required manner as detailed in association with FIG. 3 above.

Figure 6:
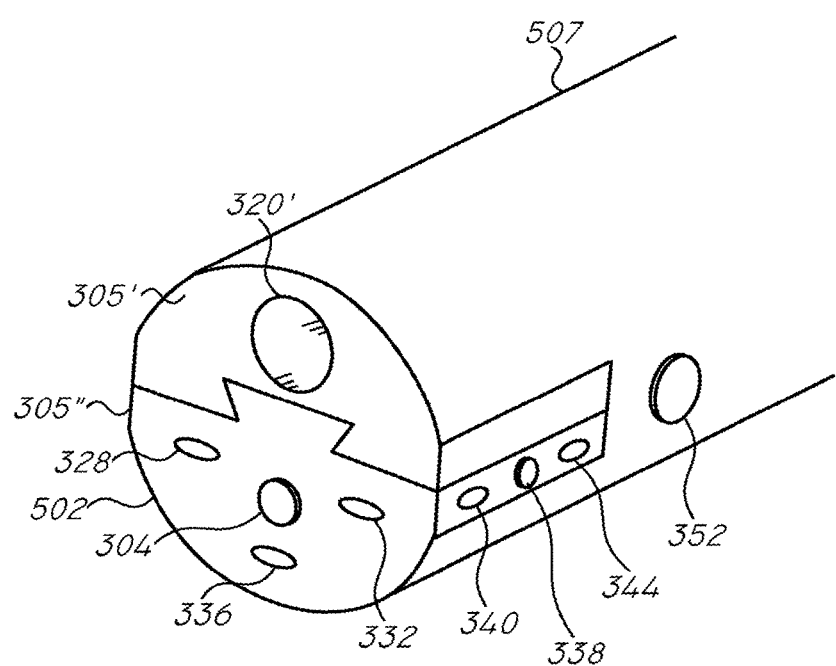
FIG. 6 shows a perspective view of a partial cross section removable tip section attached to the permanent section, in accordance with some exemplary embodiments of the disclosure.

Referring now to FIG. 6 showing a perspective view of a partial cross section removable tip section attached to the permanent section.

When removable section 502 is securely attached to permanent section 507, first part 305' of the tip section distal face which is part of removable section 502, and second part 305" of the tip section distal face which is part of permanent section 507 are substantially on the same plane with minimal or no gap therebetween, and complement each other to create the full distal face of the tip section. When removable section 502 and permanent section 507 are securely attached, switch 348 of FIG. 5 may be pressed to provide an indication to an operator of the endoscope. Removable section 502 and permanent section 507 may be released by pressing button 352, with or without providing an external release command.

When removable section 502 is securely attached to permanent section 507, utilities and equipment may be passed through a working channel formed by channel 320' and through elongated section 308' and corresponding channels in permanent section 507.

It will be appreciated that the disclosure is not limited to a single removable sections, and various implementations can be designed in which two or more removable sections are used, for example to further increase the modularity and flexibility as appropriate for each application type.

While a number of exemplary embodiments and configurations have been discussed above, those of skill in the art will recognize certain modifications, permutations, additions and sub-combinations thereof. It is therefore intended that the following appended claims and claims hereafter introduced be interpreted to include all such modifications, permutations, additions and sub-combinations as are within their true spirit and scope.

In the description and claims of the application, each of the words "comprise" "include" and "have", and forms thereof, are not necessarily limited to members in a list with which the words may be associated.

What is claimed is:

1. An endoscope comprising an elongated shaft defined by a longitudinal axis, wherein the elongated shaft comprises:
   a permanent section fixedly connected to the elongated shaft, wherein the permanent section extends cylindrically along the longitudinal axis, comprising:
      a cylindrical recess that extends along the longitudinal axis;
      a first connector positioned within said cylindrical recess; and
      a hollow cylindrical elongated protrusion extending from a distal face of the permanent section;
   a cylindrical removable section connectable to the permanent section, the removable section comprising:
      a cylindrical channel into which the hollow cylindrical elongated section protrusion from the permanent section is configured to be slidably inserted, thereby securely connecting the cylindrical removable section to the permanent section;
      an elongated section extending from a proximal face of the cylindrical removable section and having a second connector, wherein said second connector is configured to connect to the first connector positioned in the cylindrical recess;
      at least one capture device positioned in the cylindrical removable section; and
      at least one light source positioned in the cylindrical removable section;
      wherein, upon attachment of the cylindrical removable section to the permanent section, a substantially cylindrical endoscope tip is formed;
   a locking mechanism configured to form a connection between the permanent section and the cylindrical removable section; and
   a button positioned in a recess located on a side of the permanent section or cylindrical removable section, wherein the button is configured to release the locking mechanism, wherein the locking mechanism is configured to only be released if a corresponding command is provided from a control on a display device and wherein said corresponding command is configured to cause an electrical or mechanical effect required for releasing the locking mechanism.

2. The endoscope of claim 1, wherein the cylindrical removable section comprises a distal face of the endoscope tip.

3. The endoscope of claim 1, wherein the at least one capture device within the cylindrical removable section comprises a front-facing camera.

4. The endoscope of claim 1, wherein the at least one capture device within the cylindrical removable section comprises a side-facing camera.

5. The endoscope of claim 1, wherein the at least one capture device within the cylindrical removable section comprises a front-facing camera and further comprising a side-facing camera positioned in the cylindrical removable section.

6. The endoscope of claim 1, wherein the permanent section comprises at least one capture device.

7. The endoscope of claim 6, wherein at least one capture device within the permanent section comprises at least one side-facing camera.

8. The endoscope of claim 1, wherein, when the cylindrical channel of the cylindrical removable section and the hollow cylindrical elongated section protrusion from the permanent section are mated, a working channel is formed, wherein said working channel is configured to receive a surgical tool.

9. The endoscope of claim 1, wherein the cylindrical removable section comprises a first optic fiber and a first lens, and the permanent section comprises a second optic fiber and a second lens, such that the first lens is aligned with the second lens so as to transfer light between the first optic fiber and the second optic fiber.

10. The endoscope of claim 1 further comprising a switch on the permanent section, wherein the endoscope is configured to only operate when the switch is pressed by the cylindrical removable section.

11. The endoscope of claim 10 wherein an indication of a status of the switch is displayed on a display device.

12. An endoscope comprising an elongated shaft defined by a longitudinal axis, wherein the elongated shaft comprises:
    a permanent section fixedly connected to a distal end of the elongated shaft, wherein the permanent section is cylindrical and extends distally along the longitudinal axis;
    a cylindrical removable section configured to connect to the permanent section, wherein, upon connection of the cylindrical removable section to the permanent section, a substantially cylindrical endoscope tip is formed; and
    a button positioned in a recess located on a side of the permanent section or the cylindrical removable section, wherein the button is configured to release the connection between the cylindrical removable section and the permanent section, wherein the connection is only released if a corresponding command is provided from a control on a display device, and wherein the corresponding command is configured to cause an electrical or mechanical effect required for releasing the connection.

13. The endoscope of claim 12, wherein the permanent section comprises:
    a cylindrical recess that extends along the longitudinal axis; and
    a hollow cylindrical elongated protrusion emerging from a distal face of the permanent section.

14. The endoscope of claim 13, wherein the cylindrical removable section comprises a cylindrical channel into which the hollow cylindrical elongated section protrusion from the permanent section is configured to be slidably inserted, thereby securely connecting the cylindrical removable section to the permanent section.

15. The endoscope of claim 13, wherein the cylindrical removable section comprises an elongated section comprising a first connector, wherein a second connector is positioned within a recess in the permanent section, and wherein the first connector is configured to connect with the second connector when said cylindrical removable section is connected to the permanent section.

16. The endoscope of claim 12, wherein the cylindrical removable section comprises at least one capture device.

17. The endoscope of claim 16, wherein the at least one capture device within the removable section comprises at least one of a front-facing camera and a side-facing camera.

18. The endoscope of claim 12, wherein the cylindrical removable section comprises at least one light source.

\* \* \* \* \*